(12) United States Patent
Kosai et al.

(10) Patent No.: US 10,662,441 B2
(45) Date of Patent: May 26, 2020

(54) VIRAL VECTOR TARGETING CANCER STEM CELLS

(71) Applicant: KAGOSHIMA UNIVERSITY, Kagoshima-shi, Kagoshima (JP)

(72) Inventors: Kenichiro Kosai, Kagoshima (JP); Yuqing Wang, Kagoshima (JP)

(73) Assignee: KAGOSHIMA UNIVERSITY, Kagoshima-Shi (JP)

( * ) Notice: Subject to any disclaimer, the term of this patent is extended or adjusted under 35 U.S.C. 154(b) by 0 days.

(21) Appl. No.: 16/045,246

(22) Filed: Jul. 25, 2018

(65) Prior Publication Data

US 2018/0346929 A1  Dec. 6, 2018

Related U.S. Application Data

(62) Division of application No. 14/007,227, filed as application No. PCT/JP2012/002031 on Mar. 23, 2012, now abandoned.

(30) Foreign Application Priority Data

Mar. 25, 2011 (JP) ................................. 2011-068530

(51) Int. Cl.
```
G01N 33/574    (2006.01)
C12N 15/86     (2006.01)
C07K 14/705    (2006.01)
C12N 15/85     (2006.01)
A61K 35/761    (2015.01)
A61K 45/06     (2006.01)
C12Q 1/6897    (2018.01)
```

(52) U.S. Cl.
CPC ............ *C12N 15/86* (2013.01); *A61K 35/761* (2013.01); *A61K 45/06* (2013.01); *C07K 14/70596* (2013.01); *C12N 15/85* (2013.01); *C12Q 1/6897* (2013.01); *G01N 33/574* (2013.01); *G01N 33/57492* (2013.01); *C12N 2710/10332* (2013.01); *C12N 2710/10343* (2013.01); *C12N 2830/008* (2013.01)

(58) Field of Classification Search
CPC .................................................. C12N 15/86
See application file for complete search history.

(56) References Cited

U.S. PATENT DOCUMENTS

| | | |
|---|---|---|
| 2005/0125849 A1 | 6/2005 | Shmelkov et al. |
| 2005/0208466 A1 | 9/2005 | Kosai et al. |
| 2009/0181907 A1 | 7/2009 | Kamizono et al. |

FOREIGN PATENT DOCUMENTS

| | | |
|---|---|---|
| JP | 4624100 B2 | 2/2011 |
| WO | WO 03/106673 A1 | 12/2003 |
| WO | WO 2005/115476 A1 | 12/2005 |
| WO | WO 2006/076408 A1 | 7/2006 |
| WO | WO 2010/097419 A1 | 9/2010 |

OTHER PUBLICATIONS

Tabu et al. (Cell Research. 2008; 18: 1037-1046). (Year: 2008).*
Tabu et al. (Molecular Cancer. 2010; 9(39): 1-15) (Year: 2010).*
Bao et al., "Glioma stem cells promote radioresistance by preferential activation of the DNA damage response", Nature, Dec. 7, 2006, vol. 444, pp. 756-760.
Bonnet et al., "Human acute myeloid leukemia is organized as a hierarchy that originates from a primitive hematopoietic cell", Nature Medicine, Jul. 1997, vol. 3, No. 7, pp. 730-737.
Collins et al., "Prospective Identification of Tumorigenic Prostate Cancer Stem Cells", Cancer Research, Dec. 1, 2005, vol. 65, No. 23, pp. 10946-10951.
Cripe et al., "Targeting Cancer-initiating Cells With Oncolytic Viruses", Molecular Therapy, Oct. 2009 (published online Aug. 11, 2009), vol. 17, No. 10, pp. 1677-1682.
Dalerba et al., "Phenotypic characterization of human colorectal cancer stem cells", PNAS, Jun. 12, 2007, vol. 104, No. 24, pp. 10158-10163.
Eramo et al., "Identification and expansion of the tumorigenic lung cancer stem cell population", Cell Death and Differentiation, 2008, vol. 15, pp. 504-514.
Ieta et al., "Biological and Genetic Characteristics of Tumor-Initiating Cells in Colon Cancer", Annals of Surgical Oncology, 2008 (published online Oct. 12, 2007), vol. 15, No. 2, pp. 638-648.
International Preliminary Report of Patentability and English translation thereof, dated Jul. 23, 2013, for International Application No. PCT/JP2012/002031.
International Search Report, dated May 22, 2012, for International Application No. PCT/JP2012/002031.

(Continued)

*Primary Examiner* — Scott Long
(74) *Attorney, Agent, or Firm* — Birch, Stewart, Kolasch & Birch, LLP

(57) ABSTRACT

[Problem] To provide a novel and effective method for treating cancer, method for preventing cancer, and method for suppressing metastasis by targeting cancer stem cells, the methods being capable of labeling and damaging cancer stem cells; and to provide a method for damaging and a method for identifying cancer stem cells. [Solution] The present invention provides a viral vector having a promoter that is specifically expressed in cancer stem cells and that can be used for treatment and diagnosis.

Furthermore, the present invention provides a method for treating cancer, a method for preventing cancer, and a method for suppressing metastasis using this viral vector, and further provides a method for damaging and a method for identifying cancer stem cells. Furthermore, the present invention provides a labeling agent and a toxic agent for cancer stem cells containing the vector as the active ingredient, and further provides a diagnostic drug, a therapeutic drug, and a metastasis suppressant for cancer.

16 Claims, 15 Drawing Sheets

Specification includes a Sequence Listing.

(56) References Cited

OTHER PUBLICATIONS

Kemper et al., "The AC133 Epitope, but not the CD133 Protein, Is Lost upon Cancer Stem Cell Differentiation", Cancer Research, Jan. 15, 2010 (published online Jan. 12, 2010, vol. 70, No. 2, pp. 719-729.

Li et al., "Intrinsic Resistance of Tumorigenic Breast Cancer Cells to Chemotherapy", JNCI, May 7, 2008, vol. 100, Issue 9, pp. 672-679.

Liu et al., "Analysis of gene expression and chemoresistance of CD133+ cancer stem cells in glioblastoma", Molecular Cancer, Dec. 2, 2006, vol. 5, No. 67, 12 pages.

Neuzil et al., "Tumour-initiating cells vs. cancer 'stem' cells and CD133: What's in the name?", Biochemical and Biophysical Research Communications, 2007, vol. 355, pp, 855-859.

O'Brien et al., "A human colon cancer cell capable of initiating tumour growth in immunodeficient mice", Nature, Jan. 4, 2007, vol. 445, pp. 106-110.

Puglisi et al., "Isolation and characterization of CD133+ cell population with human primary and metastatic colon cancer", European Review for Medical and Pharmacological Sciences, 2009, vol. 13, Supplemental 1, pp. 55-62.

Ricci-Vitiani et al., "Identification and expansion of human colon-cancer-initiating cells", Nature, Jan. 4, 2007, vol. 445, pp. 111-115.

Shmelkov et al., "Alternative promoters regulate transcription of the gene that encodes stem cell surface protein AC133", Blood, 2004 (published online Nov. 20, 2003), vol. 103, No. 6, pp. 2055-2061.

Singh et al., "identification of a Cancer Stem Cell in Human Brain Tumors", Cancer Research, Sep. 15, 2003, vol. 63, pp. 5821-5828.

Singh et al., "Identification of human brain tumour initiating cells", Nature, Nov. 18, 2004, vol. 432, pp. 396-401.

Song et al., "Expression and clinical significance of the stem cell marker CD133 in hepatocellular carcinoma", International Journal of Clinical Practice, Aug. 2008, vol. 62, No. 8, pp. 1212-1218.

Suetsugu et al., "Characterization of CD133+ hepatocellular carcinoma cells as cancer stem/progenitor cells", Biochemical and Biophysical Research Communications, 2006, vol. 351, pp. 820-824.

Tabu et al., "Analysis of an alternative human CD133 promoter reveals the implication of Ras/ERK pathway in tumor stem-like hallmarks", Molecular Cancer, 2010, vol. 9, No. 39, 15 pages Takahashi et al., "Identification and Isolation of Embryonic Stem Cell-Derived Target Cells by Adenoviral Conditional Targeting", Molecular Therapy. vol. 14, No. 5, Nov. 2006 (published online Aug. 14. 2006), pp. 673-683.

Taniguchi et al., "β-cell neogenesis induced by adenovirus-mediated gene delivery of transcription factor pdx-1 into mouse pancreas", Gene Therapy, 2003, vol. 10, pp. 15-23.

Yin et al., "CD133 positive hepatocellular carcinoma cells possess high capacity for tumorigenicity", Int. J. Cancer, 2007, vol. 120, pp. 1444-1450.

Yuan et al., "Isolation of cancer stem cells from adult glioblastoma multiforme", Oncogene, 2004 (published online Nov. 22, 2004), vol. 23, pp. 9392-9400.

Delgado-Enciso et al., The Journal of Gene Medicine, 2007; vol. 9, pp. 852-861.

Japanese Office Action issued in Japanese Patent Application No. 2013-507161 dated Oct. 10, 2015.

Wright et al., Breast Cancer Research, 2008, vol. 10:R10, pp. 1-16.

U.S. Appl. No. 14/007,227, filed Sep. 24, 2013.

\* cited by examiner

SEQUENCE LISTING

```
<160> NUMBER OF SEQ ID NOS: 7

<210> SEQ ID NO 1
<211> LENGTH: 1192
<212> TYPE: DNA
<213> ORGANISM: Homo sapiens

<400> SEQUENCE: 1
tggaagaagg gaaagcaagc acatcttcac atggcagaag gagagacaga gcgagcaaag        60
gggaagtgcc acacactttt aaatcatcag atatcctgag aactcactca ctatcatgag       120
aacagcaagg gagaaatccg ccctcataat ccaatcacct cccactaggt ccctctccca       180
gtgaattata attcaatatg agatttggat ggggacacag agccaaacca tctaaccttg       240
ccatgtccta ctgtactttt tggaagtttt ctgaactaac atttcttgtc tagaaatata       300
cacactcaag atcaatctaa ctattaaaaa caaaaaatgc ttattttcca gtacctgttt       360
tatgttagat tctggggtaa aaagaaaaag gtactgactt aatgttcctg tctatcattc       420
atttgtagct tgtgcatcca tcctttcatc tgtctatcca tatcacaaac atgtattaaa       480
cacctgctgt atgctagaca ccatcctgaa ggtgcatttc ttccctaagt cttttttttg       540
cctgccggag agtacagtat tctcaattca agataagaag tggtgaataa gagtgaagtg       600
caaattggtg aggacactta gacaccgagt gattacttct gacaggtttc caccactcag       660
```

```
ctaagtagca aggtgaagac tccgaggttg agttgtaact cacagagcgg gaagaccaat    720
aggcagtgag aaaagaagtt gcagtggctt cacgttatag cagatgcctg tgtgtacaca    780
tgggagcgaa tatggcttta tgctgttttt caaccgcttc agccactagc attggtactg    840
ctgcacacta aggatccaaa tgattgtttt tttgttttt gttttgtttt gttttgtttt    900
gttttgtttt aaattgcatt gggattaggc aacagaaggg tctaatgcgg ccgggatgag    960
acaggagagt ttttaggagg gtagctgcat tctaagtaag ggactctgcg gggggaaaag   1020
aggcgcaagc gttgcaagaa gggagtgcag ggggttgagc aggcacctct acaggaaatg   1080
gatgctgtcc aggtgctggt gggcgcccca gggctacgtg gcgaagcagc tcagccggtc   1140
caatcagagt gcgtccaggg ctcgggtttc gcgatcttta agtgactgag gc           1192
```

```
<210> SEQ ID NO 2
<211> LENGTH: 253
<212> TYPE: DNA
<213> ORGANISM: Homo sapiens

<400> SEQUENCE: 2
gtgagtatgt ttaaggaatc cttctccatta cggcggcccc ataacctaggt ccccgtccgg    60 gacagaggaa gccgcaacgg gtccccccgg gcacccgggc ctttctcctg cctcccgcca   120
cgtccgaggg tccggccgca gcgccgcctg agccctccg cggccggcag tgggaggcgg   180
gctctccgaa agccgtcgcg gtggtccag aagccgggtc ataaataatt cacgagccag   240
ggtctggcga gct                                                      253
```

```
<210> SEQ ID NO 3
<211> LENGTH: 199
<212> TYPE: DNA
<213> ORGANISM: Homo sapiens

<400> SEQUENCE: 3
gtgagtagct gggtcctcat cccggagcga gagaggcatc tgctgaccag gcgcggggct    60
gagcgcactc cttccactgt actggggtg tacagtgagg agtggacggg ttcgctctgc   120 gccccccttta ccctagccat ctgcgccgcc tccctggccc ctcagcaggt ggtgcgggcc   180
cggacagcgg ctgggggcc                                                199
```

```
<210> SEQ ID NO 4
<211> LENGTH: 1451
<212> TYPE: DNA
<213> ORGANISM: Homo sapiens

<400> SEQUENCE: 4
gacagacccc agatagcctt ccagctgcgt gccaggtgct ttacctatta gatcgctagc    60
ctgcgaaccc tatgcgaaat cctcctttga cagaggagca aagaagggt tggagaattc   120 aaacaactgt catcttggca gagttagtaa ggggaccag agccccctta ctgttgctgt   180
tgtctgtcta ttcagcagtg cccttttagtt tattcttgtt ttttttttca tgtgttccat   240 aattttttc taaacttcct tctgatttct aaacttttct aaacttcttt ctgatttcta   300
aacttccttc tgatttttat acgagacagt tcctttgtgt tttagtacaa tgaggtgaac   360
aaatgcatca gaggacaagc tgaaaacttt aaaccaagtt ggtactgttt aaaatataaa   420 ggaaatagg ttttcaggga gcaaagagct atttctgaga tttgttaagg gtcaagatac   480
tttgttaaaa cagtggaagc tgagtcgggg gtaattttta tcagataaag gacttcttgg   540
```

| | |
|---|---|
| attctgtaag ttgcctgttc actctgatgg tagtttcttt tgctctgcag aagctctta | 600 |
| gtttaattag atcccatttg tcaattttgg cttttgttgc cattgctttt ggtgttttag | 660 |
| acatgaagtc cttgcccatg cctatgtcct gaatggtatt gcctaggttt tcttctaggg | 720 |
| tttttatggt tttaggtcta acatttaagt ttttaatcca tcttgaatta attttgtat | 780 |
| aaggtgtaag gaagggatcc agtttcagct ttctacatat ggctagccag gtttcccagc | 840 |
| accgtttgtt gggaattgaa caatgaaaac acttggacac aggaagggga acatcacaca | 900 |
| ccggggcctg ttgtcaggtg gcgggagtgg ggagggatag cattaggaca tatacctaat | 960 |
| gtaaatgacg agttaatagg tgcagcacac cgacatggca catgtataca catgtaacaa | 1020 |
| acatgcacat tgtgcacatg taccctagaa cttaaagtat aataaaaaaa tatatataca | 1080 |
| tatacatata tatatgtata tgtatatata taaaaggact tcttgaaagg atggtccctg | 1140 |
| ggtggcttag gtaagtggca gcaaggctgg ctagccaggc ttaggaatct aggacatgcc | 1200 |
| acaggacccc tgatgggtgg gtggctgcgg ctgccagaac aggaccctgg atgtggctac | 1260 |
| tggcattgct gccatcattg ctggaatgaa ttagatactg tcctgcttca gagtgcgcag | 1320 |
| gcccaggccc agaagaaagc ttctgattgg cccagcatgg ctcagctcca ccaggacaca | 1380 |
| gtttgggcgc ctcagctgac ctcacaatgc aaggcagggc tgcctcccac ccagctcaca | 1440 |
| aacgtggtct c | 1451 |

<210> SEQ ID NO 5
<211> LENGTH: 1368
<212> TYPE: DNA
<213> ORGANISM: Homo sapiens

<400> SEQUENCE: 5

| | |
|---|---|
| gcatgtctgt ctctgtgtcc aaattttccc ttttaaaaa ggcactagcc ataatggatt | 60 |
| agggttcacc ataatgagtt catttaact aaacaatta cctctataaa caccctgtct | 120 |
| ccaaataagg tcacattctc tggtactggg gattgggact tcaatgtatg agtgttttgg | 180 |
| ggcacaccag ttagcccgta acagggtagc tgcaatgatg acaggaaatc agggatgggt | 240 |
| aagcattcat aaatgtcact ctcctagagg aaagggaggc ttcctttcgg ggacatttt | 300 |
| tgtcctcatc ttgcctgggt tatagaagca actcacatag gattttgct gggtgactcc | 360 |
| ctaccctact gcagatgatt ccactgtaca ctctgggagg gacatgtgct gtaaactcag | 420 |
| cataaaatgt catagtggtc ccaactcagc ataaaatgtc atagggcacc ccggctgggt | 480 |
| gaattcttcc agaccctgtt ttctcttcct catgcttcag acctcttcat ttcacaagca | 540 |
| gtctgttgaa gtaaccaaac tcccaggccc agagtcagcc aatctgcatt tcaacccccc | 600 |
| acctccattc ctcagcaatg gcccttcatc ttggaaatca gaattaatca cagcctctat | 660 |
| gcctgaatta aagtttgctc ttgtatcttc tttaccaagt ttacatatac tcaatattgg | 720 |
| tgtatacaac tatgtaatgc agtatgacct ctctctgtct ctgttctcct ggcaactcat | 780 |
| tcaggctcca ttcccttcat atcccacttg aatttgcact actctgcacc actgacttta | 840 |
| gaatctgtct tgtaaatagg gtcagagttc ctcagccaga tcccgatggg taaaaggaac | 900 |
| catgtcccca ccctgagttg agcaggtctt caagaaaccc tcttgtgagt ccactctgcc | 960 |
| ccaaagctgc ctcccaaaga tgcagcatct gtcctggcag agtgtgggca ggaaggctgc | 1020 |
| cttgccaggc tcctgactcc cagtgctgcg tggtgctgat gagctgagct gatctttgag | 1080 |
| gggccagacc aggtgaaagt tcccacccta agcagctcag ggcagggaca gaccaaatcc | 1140 |
| aagtgcacca atgggggcca tgagaaaccc tcctgtgggg atatctgtga tctcaggaat | 1200 |

```
gaccctgaga ggacactgct ctgatgctct gatgagactg aggggggattc caagcttcca      1260 gggtgctggg cagtgtctcc ccagagagtg gctgttccca gtgtcaatca ggcaggaagg      1320
gtagaatgct gggacaggaa gtagcttgga ggtgggcctt aggctggt                   1368

<210> SEQ ID NO 6
<211> LENGTH: 1000
<212> TYPE: DNA
<213> ORGANISM: Mus musculus

<400> SEQUENCE: 6
tgactcggaa tggaagtgtc ccataagatg gatgacctga tgagcttatt agaaaagcag        60
atttcagttt ctgtttgtcc atgaccctga ggttcttctc ctctttgggc ttaggataga       120
tggaatgatg gatgcctgga gtgtgatctg tttgcaaaca ggatgtaagg aaggggtact       180
gtcagtgtta gaaggacagc aggaaacttt aaaaaactaa gcactattcc gtggctgggg       240
gcctctttgg caccagccgg agcttgggag gacaagccgg agcatcagag ccctgctgtg       300
ctggtcagat ggactctaag ggaaaagact gagttgaatt ctggccagac tgtactaaaa       360
tcccttctgc acatgttccg tcatctataa ggtgggatta tgccttaaga gcatgtggaa       420
tgtacctgga attcagtgag tgatgaacat ctgtttccaa gaataaacag cttcctgaac       480
cgtgcctggt gtttcttgat cctggaaagg actgtcctct gaatcatcct atcttggagg       540
aaggagcctc ttcctagtcc ctacctgtag ctccggagca ggctgttagc ttgggttcca       600
cctcgttagg cctaagtgtt taattctaag ccatgtcact tcctctgggg tgggctcctg       660
gggaactggt tgtctctgag taatcagtgt tctttctctc cctcccaggg atggtacttt       720
gagtgaatga ccaccttgga gaccgttctt ctgtttccct tgttaccagc caggaggcag       780
aagagtccac cggtccagga aagacccatt tcccttgagt ttccagaaag tacctcatgc       840
ttgagagatc aggccaacaa ctatggctct cgtcttcagt gccctgctgt tactggggct       900
gtgtggaaag atctcttcag aaggtcagcc tgcattccat aacactcctg gggctatgaa       960
ttatgaattg cctaccacca aatatgagac ccaagatacc                            1000

<210> SEQ ID NO 7
<211> LENGTH: 1000
<212> TYPE: DNA
<213> ORGANISM: Mus musculus

<400> SEQUENCE: 7
acatatccat tgcaactcat gaatgattct ctcctgtttt gttttttaact tttcttttta      60 cactgatttt ctatttagac actaaaacat ataggggtgc ttattccccc tggatacatt      120
tacctgtgaa ccagctattc cggtgtcata gctgggtacc taacttactt ccatatgtga      180
agtgtgctaa acacaaacca gtttacagaa gagatgtatt ttgtgtatag taaactgtat      240
atataccctt ttaccacagt cagttttttta aacaaatgaa tactctagat ttttcttcta     300
aatgaggtta ctgttggggt ggttgtgacc tagtgatgct gtagaaagga gtctgcattc      360
actaaaagtg tgtcaaccta gagcaggcaa tgcccttcct tgtggatttc tgtctgctcg      420
ttttggagct acctgcggtt tagaaataga attcaagaac aatcacgagg tttcccactt      480
gatgccactg ccaaagtcag aacaagggat cttgagagaa ggaactgtcg ctcagctggg      540
agcggaatca ttatcgcaat cacaggtcct ggttcacagt ttagtggcac tctctggttt      600
gtaagaatgg gcattacgtt cagtgtcatc tggtcatctg tgatgtgtgt catcagcctg      660
```

```
tcctgatgtt gagatttaaa ataaagcatg aatgaacaga gcttttggtg tttggtcctt    720
aaaacacaca gaagtgtaaa gtgaatttgc gtttgctgtg gttatccttg ttggccttca    780
cctttccaaa aatgagcagt gggggaaagc tggtcaggtc aaagagactg tgtcctgcag    840
gtaaagggtt tgttctacac cagcctttcc gtatgcgacc ccggccctga ttcatttcaa    900
tttaaaggag cgtggcaagt gtggcttcct tgagtggcca gagcttgcag tgcctgtgat    960
gaagcccatg ctctgattag tcccctgctc tccaggattg                         1000
```

VIRAL VECTOR TARGETING CANCER STEM CELLS

This application is a Divisional of copending application Ser. No. 14/007,227 filed on Sep. 24, 2013, which is the U.S. National Phase of PCT/JP2012/002031, filed Mar. 23, 2012, and which claims priority under 35 U.S.C. § 119(a) to Application No. 2011-068530 filed in Japan, on Mar. 25, 2011, the entire contents of all of which are expressly incorporated by reference into the present application.

TECHNICAL FIELD

The present invention relates to a recombinant adenoviral vector comprising a cancer stem cell-specific promoter. In particular, the present invention relates to an adenoviral vector capable of replicating specifically in cancer stem cells. In addition, the present invention relates to a method for identifying cancer stem cells, and a diagnostic method and a therapeutic method for cancer, each of which utilizes the aforementioned vector. The present invention relates to a diagnostic agent and a therapeutic agent for cancer, each of which comprises the adenoviral vector as an active ingredient.

BACKGROUND ART

In recent years, the presence of cancer stem cells in several types of cancers such as brain tumor (see Non Patent Literatures 1 to 4) and colon cancer (see Non Patent Literatures 5 to 9) has been reported. Cancer stem cells are defined as a small number of cells among cancer cells that constitute cancer, which have the properties of stem cells and have an ability to form a tumor. Cancer stem cells have the following characteristics: 1) a low division rate and a low replication rate; 2) a high self-replicating and self-repairing ability; 3) the cancer stem cells produce a large number of cancer cells around themselves as a result of differentiation, while maintaining themselves by self-replication in cancer tissues; 4) resistance to anticancer agents and resistance to radiotherapy (see Non Patent Literatures 4, 10 and 11). However, it is not essential for cancer stem cells to have all of the properties 1) to 4), if the cancer stem cells have the properties of stem-like cells. It is important that such a cancer stem cell is a main cause of the malignancy of cancer. Thus, the cancer stem cell is also referred to as a "tumor-initiating cell" or a "cancer-initiating cell" (a cancer initiating cell, or an initiating cell of tumor or cancer) (see Non Patent Literature 12).

A cancer stem cell has attracted attention as an important therapeutic target in treatment of cancer. The cancer stem cell hypothesis had already been proposed in the 1970s. In recent years, it has also been elucidated that the presence of cancer stem cells is associated with the resistance to various types of therapy, recurrence, and malignant alteration of cancer. However, a main body of such cancer stem cells remains unknown, and currently, there has been little progress in the study regarding biological analyses and cancer treatments (in particular, cancer stem cell-specific treatments) that target cancer stem cells.

For solid cancer, in particular, brain tumor, CD133 has been reported as a cancer stem cell marker that is expressed on the cell surface (see Non Patent Literatures 1 to 4). Human CD133 was confirmed to be an epitope expressed in CD34+ hematopoietic stem cells in 1997 (see Non Patent Literature 13). CD133 is a five-transmembrane type membrane glycoprotein that is also referred to as prominin 1 (PROM 1), and it includes many spliced isoforms and the expression thereof depends on tissues. A CD133 ligand and a signal downstream thereof have not yet been reported, and the functions thereof have been unknown. It has been reported that CD133 is a marker for hematopoietic progenitor cells and vascular endothelial progenitor cells, and at the same time, CD133 is a cancer stem cell marker for brain tumor (see Non Patent Literatures 1 to 4), prostate cancer (see Non Patent Literature 14), colon cancer (see Non Patent Literatures 5 to 9), lung cancer (see Non Patent Literature 15), and hepatic cancer (see Non Patent Literatures 16 to 18).

It has been reported that CD133 is expressed in a tissue-dependent manner by at least 5 types of promoters. It has been demonstrated that promoters 1 and 2 had activity while promoters 3 to 5 did not have particularly high activity as a result of a reporter assay in which the human colon carcinoma cell line Caco-2 cell and the human teratocarcinoma cell line NT-2 were used (see Non Patent Literature 19). On the other hand, it has been reported that promoters 1 to 4 had almost no activity, and that promoter 5 had activity as a result of the analysis of the activity of CD133 promoters in the human colon carcinoma cell line Caco-2 and the human synovial sarcoma cell line Fuji (see Non Patent Literature 20). In these reports, all of the methods use a pGL3 enhancer vector, which means the activity of the CD133 promoter was enhanced by the enhancer, nevertheless relatively high promoter activity was not observed. Especially, despite it has been known that the Caco-2 cells strongly express CD133, it has also been known that the promoter activity of CD133 (in particular, promoters 1 to 4) is not so high even in a case in which the Caco-2 cells are used with the pGL3 enhancer vector. Moreover, the activity of CD133 promoters in cancer stem cells has not yet been known so far.

It has been generally known that promoters which are specific to tissues or cells such as stem cells have extremely lower activities than the constitutively and ubiquitously active promoters which are widely used infor inducing transgene expression, such as RSV promoter, CMV promoter or CA promoter. In using such tissue/cell-specific promoters for treatment or diagnosis, in many cases these promoters by themselves cannot be used for the treatment or the diagnosis due to its low promoter activity in cells of interest, and thus, it has been recognized that a means to enhance the promoter activity is necessary (see Patent Literature 1 and Non Patent Literature 21).

Virus vectors that are able to replicate specifically in cancer (conditionally replicating viruses: CRA) have been known, such as viral vector an adenoviral vector which lack the Rb-binding region in the E1 region (E1AΔ24) or which lack the p53-binding region in the E1 region (E1BΔ55), and an adenoviral vector in which an endogenous promoter of an E1 gene is substituted with a promoter that highly express specifically in cancer. Examples of the latter viral vector that has been reported include an adenoviral vector employing a urokinase-type plasminogen activation receptor promoter (see Patent Literature 2), an adenoviral vector employing a PEG3 promoter (see Patent Literature 3), and an adenoviral vector employing a survivin promoter (see Patent Literature 4). Since a cancer specific replicating adenoviral vector has oncolytic properties (see Non Patent Literature 22), it is considered to be effective for the treatment of cancer. Moreover, once viruses are infected/transfected in some cancer cells upon administration of the viral vector, they are amplified in the cancer cells, viral vectordestroy the cancer cells, and are further infected/transfected to peripheral or distant cancer cells. Accordingly, by loading a gene, CRA is also considered to be a useful tool for gene delivery.

Furthermore, treatment with a viral vector targeting cancer stem cells has also been reported (Patent Literature 23).

CITATION LIST

Patent Literature

Patent Literature 1: International Publication No. WO 2010/097419
Patent Literature 2: International Publication No. WO 2006/076408
Patent Literature 3: International Publication No. WO 2005/115476
Patent Literature 4: Japanese Patent No. 4624100

Non Patent Literature

Non Patent Literature 1: Singh S K, et al. Nature 2004; 432: 396-401
Non Patent Literature 2: Singh S K, et al. Cancer Res 2003; 63: 5821-8
Non Patent Literature 3: Yuan X, et al. Oncogene 2004; 23: 9392-400
Non Patent Literature 4: Liu G, et al. Mol Cancer 2006; 5: 67
Non Patent Literature 5: Dalerba P, et al. Proc Natl Acad Sci USA 2007; 104: 10158-63
Non Patent Literature 6: Ricci-Vitiani L, et al. Nature 2007; 445: 111-5
Non Patent Literature 7: Puglisi M A, et al. Eur Rev Med Pharmacol Sci 2009; 13 Suppl 1: 55-62
Non Patent Literature 8: O'Brien C A, et al. Nature 2007; 445: 106-10
Non Patent Literature 9: Leta K, et al. Ann Surg Oncol 2008; 15: 638-48
Non Patent Literature 10: Bao s, et al. Nature 2006; 444: 756-60
Non Patent Literature 11: Li X, et al. J Natl Cancer Inst 2008; 100: 672-9
Non Patent Literature 12: Neuzil J, et al. Biochem Biophys Res Comm. 355: 855-859, 2007
Non Patent Literature 13: Bonnet D, et al. Nat Med 1997; 3: 730-7
Non Patent Literature 14: Collins A T, et al. Cancer Res 2005; 65: 10946-51
Non Patent Literature 15: A Eramo, et al. Cell Death and Differentiation (2008); 15: 504-514
Non Patent Literature 16: W Song, et al. International Journal of Clinical Practice (2008) 62 (8): 1212-1218
Non Patent Literature 17: Atsushi Suetsugu, et al. Biochemical and Biophysical Research Communications (2006) 351: 820-824
Non Patent Literature 18: Shengyong Yin et al. Int. J. Cancer (2007) 120: 1444-1450
Non Patent Literature 19: Shmelkov S V, et al. Blood 2004; 103: 2055-61
Non Patent Literature 20: Kouichi Tabu, et al. Molecular Cancer 2010; 9: 39
Non Patent Literature 21: Tomokoyuki T, et al. Molecular Therapy 2006; 14 (5): 673-683
Non Patent Literature 22: Toth K, et al. Gene Ther. 2003; 10: 15-23
Non Patent Literature 23: Timothy P Cripe, et al. Molecular Therapy, 17 (10): 1677-1682

SUMMARY OF INVENTION

Technical Problem

An efficient therapeutic method or the like that targets cancer stem cells has not yet been reported. A method for specifically identifying cancer stem cells using an antibody or the like requires contact of the antibody or the like with the cell surface, and thus it cannot visualize cancer stem cells present inner of cancer tissues. Therefore, it has been desired to develop a more effective visualizing method which can identify inner cancer stem cells of cancer tissues.

Accordingly, the present invention objects to provide a novel and efficient methods for treating cancer and for visualizing cancer stem cells, which target cancer stem cells.

Solution to Problem

The present inventors have conducted intensive studies regarding a promoter that has high activity specifically in cancer stem cells and can be used for therapeutic purpose or diagnostic purpose. As a result, the inventors have unexpectedly found that, although the expression level of CD133 in cancer stem cells is equivalent to or lower than that in CaCo-2 cells, the activity of a CD133 promoter is high in cancer stem cells and that it is enough for using in treatment and diagnosis by itself. In addition, the present inventors have applied the CD133 promoter to a conditionally replicating adenovirus (hereinafter referred to as "CRA") to produce a vector capable of replicating specifically in cancer stem cellsviral vector and studied on the produced vector. As a result, the inventors have found that CRA in which a CD133 promoter is operably linked to a nucleic acid encoding a protein that is essential for replication of virus (such as E1A and E1B) in the viral genome (hereinafter referred to as "CD133-CRA") replicates specifically in cancer stem cells. Moreover, the present inventors have confirmed that a vector that replicates specifically in cancer stem cells can infect cancer stem cells and replicate in said cancer stem cells.

Since the vector of the present invention replicates specifically in cancer stem cells existing in cancer tissues, by inserting a exogenous marker gene into the present vector, the vector can be used for identifying the cancer stem cells in the cancer tissues. Furthermore, since the vector of the present invention not only replicates specifically in cancer stem cells but also maintains an ability to finally destroy the cancer stem cells, it is useful for a treatment that targets cancer stem cells.

Therefore, the present invention relates to a promoter that is activated specifically in cancer stem cells and a viral vector comprising said promoter. In addition, the present invention also relates to a viral vector capable of replicating specifically in cancer stem cells. Moreover, the present invention also provides a method for visualizing cancer stem cells, and a diagnostic method and a therapeutic method for cancer, in each of which the aforementioned vector is used. Furthermore, the present invention provides an agent for visualizing cancer stem cells, and a diagnostic agent, a metastasis-suppressing agent and a therapeutic agent for cancer, each of which comprises a vector capable of replicating specifically in cancer stem cells as an active ingredient. Specifically, the present invention provides CD133-CRA as a vector capable of replicating specifically in cancer stem cells. In the present invention, a preventive method, a metastasis-suppressing method and a therapeutic method for cancer are based on the suppression of proliferation or the killing or damaging of cancer stem cells that cause development of cancer.

Specifically, the present invention relates to the following inventions:

(1) A viral vector comprising a CD133 promoter operably linked to a desired gene, wherein said viral vector can express said desired gene specifically in a cancer stem cell.
(2) The viral vector of (1), wherein the desired gene is a gene encoding a protein which is essential for replication of virus and the viral vector can replicate specifically in a cancer stem cell.
(3) The viral vector of (2), wherein the viral vector is oncolytic.
(4) The viral vector of (2) or (3), wherein the viral vector is adenovirus, herpes simplex virus, myxoma virus, reovirus, vesicular stomatitis virus, Newcastle disease virus, vaccinia virus, RS virus, Sendai virus, measles virus, Coxsackie virus, or Seneca Valley virus.
(5) The viral vector of (2) or (3), wherein the viral vector is adenovirus.
(6) The adenoviral vector of (5), wherein the desired gene is an adenovirus E1A or E1B gene.
(7) The adenoviral vector of (6), wherein the E1A is an E1A lacking the Rb-binding region (E1AΔ24) or the E1B is an E1B lacking the p53-binding region (E1BΔ55K).
(8) The viral vector of any one of (2) to (7), further comprising a marker gene or a cytotoxic gene.
(9) The viral vector of any one of (2) to (8), further comprising an exogenous cancer-specific promoter.
(10) The adenoviral vector of (6) or (7), wherein the adenoviral vector is selected from the following (a) to (c):
(a) an adenoviral vector having the following transcription units:
  (a1) a CD133 transcription unit consisting of a CD133 promoter and an E1A gene or E1AΔ24 gene operably linked downstream of said promoter,
  (a2) a transcription unit consisting of a eukaryotic cell promoter, a cancer-specific promoter or CD133 promoter, and an E1B gene or E1BΔ55K gene operably linked downstream of said promoter, or a transcription unit consisting of an E1BΔ19K gene operably linked downstream of a cancer-specific promoter, and
  (a3) optionally, an additional transcription unit consisting of a eukaryotic cell promoter, a cancer-specific promoter or CD133 promoter, and a marker gene or cytotoxic gene operably linked downstream of said promoter;
(b) an adenoviral vector having the following transcription units:
  (b1) a transcription unit consisting of a eukaryotic cell promoter, a cancer-specific promoter or CD133 promoter, and an E1A gene or E1AΔ24 gene operably linked downstream of said promoter,
  (b2) a CD133 transcription unit consisting of a CD133 promoter and a E1B gene or E1BΔ55K gene operably linked downstream of said CD133 promoter, and
  (b3) optionally, an additional transcription unit consisting of a eukaryotic cell promoter, a cancer-specific promoter or CD133 promoter, and a marker gene or cytotoxic gene operably linked downstream of said promoter; and
(c) an adenoviral vector having the following transcription units:
  (c1) a transcription unit consisting of a eukaryotic cell promoter, a cancer-specific promoter or CD133 promoter, and an E1A gene or E1AΔ24 gene operably linked downstream of said promoter,
  (c2) a transcription unit consisting of a eukaryotic cell promoter, a cancer-specific promoter or CD133 promoter, and an E1B gene or E1BΔ55K gene operably linked downstream of said promoter, and
  (c3) a CD133 transcription unit consisting of a CD133 promoter and a marker gene or cytotoxic gene operably linked downstream of said CD133 promoter.
(11) The viral vector of (1), wherein the desired gene is a marker gene.
(12) The viral vector of (11), further comprising an exogenous cancer-specific promoter.
(13) The viral vector of (11) or (12), further comprising a cytotoxic gene.
(14) The viral vector of (1), wherein the desired gene is a cytotoxic gene.
(15) The viral vector of (14), further comprising an exogenous cancer-specific promoter.
(16) The adenoviral vector of (14) or (15), further comprising a marker gene.
(17) The viral vector of any one of (11) to (16), wherein the viral vector is oncolytic virus.
(18) The viral vector of any one of (11) to (17), wherein the viral vector is adenovirus, herpes simplex virus, myxoma virus, reovirus, vesicular stomatitis virus, Newcastle disease virus, vaccinia virus, RS virus, Sendai virus, measles virus, Coxsackie virus, or Seneca Valley virus.
(19) The viral vector of any one of (1) to (18), wherein the CD133 promoter is any one of nucleic acid molecule selected from the following (i) to (iv):
(i) a nucleic acid molecule comprising the nucleotide sequence of any one of SEQ ID NOS: 1 to 5,
(ii) a nucleic acid molecule comprising a nucleotide sequence having 85% homology to any one of SEQ ID NOS: 1 to 5,
(iii) a nucleic acid molecule which can hybridize under stringent conditions with the nucleic acid molecule having the nucleotide sequence of any one of SEQ ID NOS: 1 to 5 or having complement of said sequence, and
(iv) a nucleic acid molecule having a nucleotide sequence of any one of SEQ ID NOS: 1 to 5, wherein a part of nucleotide is substituted or deleted, or additional nucleotide is added or inserted.
(20) A therapeutic agent, metastasis-suppressing agent or prophylactic agent or diagnostic agent for cancer, comprising the viral vector of any one of (1) to (19).
(21) An agent for visualizing cancer stem cells, comprising the viral vector of any one of (1) to (19).
(22) The therapeutic agent or prophylactic agent or diagnostic agent of (20), further comprising one or more agents selected from the following (i) and (ii):
(i) a drug for decreasing antiviral action, and
(ii) an anticancer agent;
wherein said agents are administered simultaneously, continuously, or separately at certain intervals.
(23) A method for visualizing cancer stem cells, comprising a step of administering the viral vector of any one of (1) to (19) to a patient in need thereof.
(24) A method for diagnosing cancer, comprising a step of administering the viral vector of any one of (1) to (19) to a patient in need thereof.
(25) The method of (23) or (24), wherein the viral vector has a marker gene.
(26) A prophylactic method, metastasis-suppressing method or therapeutic method for cancer, comprising a step of administering the viral vector of any one of (1) to (20) to a patient in need thereof.

(27) The prophylactic method, metastasis-suppressing method or therapeutic method of (26), further comprising a step of infecting the cancer stem cells of the patient with the viral vector.

(28) The method of (26) or (27), wherein the viral vector has a cytotoxic gene.

(29) The method of any one of (23) to (28), wherein the desired gene is a gene encoding a protein essential for replication of virus and the viral vector can replicate specifically in a cancer stem cell.

The CD133 promoter that can be used in the present invention is not particularly limited, as long as it is a nucleic acid molecule having a sequence reported as a promoter of CD133 (which is also referred to as AC133 or PROM1). For example, mouse CD133, rat CD133 and human CD133 have been reported. Examples of the CD133 promoter include, but are not limited to, human CD133 promoters 1 to 5 disclosed in Shmelkov S V, et al., Blood 2004; 103: 2055-61, and in GenBank Accession Nos. AY275524, AY438641 and AY438640. Specific examples of the promoter of the present invention include human CD133 promoter 1 (pr1; SEQ ID NO: 1), promoter 2 (pr2; SEQ ID NO: 2), promoter 3 (pr3; SEQ ID NO: 3), promoter 4 (pr4; SEQ ID NO: 4), and promoter 5 (pr5; SEQ ID NO: 5). CD133 promoters from other animal species (e.g. mouse Prominin-1 promoter 1 (SEQ ID NO: 6), promoter 2 (SEQ ID NO: 7), or promoter 3 (SEQ ID NO: 8)) (Kemper K, Tol M J P M, Medema J P (2010) Mouse Tissue Express Multiple Splice Variants of Prominin-1. PloS ONE 5 (8): e12325) may also be used.

Moreover, in addition to the above-mentioned promoters, the "CD133 promoter" may also be a nucleic acid molecule having a nucleotide sequence having 85%, 90%, 95%, or 98% homology with the nucleotide sequence of any one of SEQ ID NOS: 1 to 7. Such sequence homology can be determined, for example, using BLAST. Furthermore, in addition to the above-mentioned promoters, the "CD133 promoter" may also be a nucleic acid molecule hybridizing under stringent conditions with the nucleic acid molecule comprising the nucleotide sequence having any one of SEQ ID NOS: 1 to 7 or having complement thereof. Herein, the expression "hybridizing under stringent conditions" means that hybridization is performed by the method described in Frederick M. Ausubel et al, "Current Protocols in Molecular Biology" (2011). More specifically, a nucleic acid molecule is allowed to react with DNA immobilized on a nitrocellulose membrane at 65° C. in a solution of 0.5 M NaHPO$_4$, 7% sodium dodecyl sulfate (SDS) and 1 mM EDTA, and thereafter, the resultant is washed with 0.1 to 0.5×SSC (15 to 30 mM NaCl, 1.5 to 3 mM sodium citrate, pH 7.0) and 0.1% SDS at 65° C. to 68° C. several times so as to perform hybridization. The "CD133 promoter" includes a nucleic acid molecule having a nucleotide sequence of SEQ ID NOS: 1 to 7, wherein a part of nucleotide are substituted or deleted or additional nucleotide(s) are inserted or added. When nucleic acids are deleted, added or inserted, the deletion, addition or insertion are within a number that does not cause frameshift of downstream gene. Examples of a number of such substitution, deletion, addition and insertion includes 1 to 50 nucleotides, 1 to 20 nucleotides, 1 to 10 nucleotides, and 1 to 3 nucleotides. In addition, two or more types of mutations from such substitution, deletion, addition and insertion may be included. Nucleic acids are preferably substituted, deleted, added or inserted in a location other than a transcription factor-binding region. Such a transcription factor-binding region may be investigated using a program for predicting a transcription factor-binding region, such as TFSEARCH and Alibaba, or may also be learned from the descriptions of Shmelkov S V, et al. Blood 2004; 103: 2055-61 (FIG. 3, etc.).

Said nucleic acid molecule having 85%, 90%, 95% or 98% homology with the nucleotide sequence of any one of SEQ ID NOS: 1 to 7, said nucleic acid molecule hybridizing under stringent conditions with the nucleic acid molecule comprising the nucleotide sequence having any one of SEQ ID NOS: 1 to 7 or having complement thereof, and said nucleic acid molecule having the nucleotide sequence shown in any one of SEQ ID NOS: 1 to 7 wherein a part of nucleotides are substituted or deleted or additional nucleotides are added or inserted preferably have promoter activity equivalent to CD133. Herein, the term "promoter activity equivalent to CD133" means that a promoter activity is high under conditions in which a wild-type CD133 promoter activity is high, and simultaneously that a promoter activity is low under conditions in which a wild-type CD133 promoter activity is low. The promoter activity equivalent to CD133 generally means qualitatively equivalent to the activity of a wild-type CD133 promoter. However, it may also mean quantitatively equivalent to or even higher than the activity of a wild-type CD133 promoter.

Further, in the present specification, the term "CD133 promoter" includes a fragment of the above described CD133 promoter, as long as the fragment maintains promoter activity equivalent to CD133. Such a fragment of the CD133 promoter has at least one transcription factor-binding region of the CD133 promoter, and preferably has all of the transcription factor-binding regions of the CD133 promoter. The transcription factor-binding region can be determined by the above described method. For instance, fragments of the CD133 promoter of the present invention may be fragments of human CD133 promoter 1 (pr1; SEQ ID NO: 1), promoter 2 (pr2; SEQ ID NO: 2), promoter 3 (pr3; SEQ ID NO: 3), promoter 4 (pr4; SEQ ID NO: 4), and promoter 5 (pry; SEQ ID NO: 5); and mouse CD133 promoter 1 (SEQ ID NO: 6), promoter 2 (SEQ ID NO: 7), and promoter 3 (SEQ ID NO: 8).

Herein, the expression, the CD133 promoter "is operably linked" to a desired gene in a viral genome, means that the CD133 promoter is located upstream of the desired gene, so that it can operate transcription of said gene.

Herein, the "viral vector" is a virus capable of incorporating exogenous DNA or RNA into a gene and viral vector not particularly limited as long as it is safely administered to a target animal (e.g. a human). The viral vector of the present invention may be either a DNA virus or an RNA virus. Preferably, the viral vector of the present invention is a virus that is neither infectious nor self-replicable in cells other than cancer cells (preferably, cancer stem cells). Moreover, the viral vector is preferably a virus that has oncolytic properties or can acquire such oncolytic properties as a result of genetic recombination. When the viral vector of the present invention is used for therapeutic purpose, it preferably has cytolytic properties. The term "cytolytic properties" means the ability of a viral vector to lyse cells in which the viral vector can replicate (e.g. cancer cells, cancer stem cells) and to release the viruses outside of the cells on infecting said virus-replicable cellsviral vector.

Herein, the term "oncolytic virus" means a virus having an ability to lyse tumor cells. Preferably, the oncolytic virus shows toxicity to human cancer cells but not to normal human cells. The tumor specificity of virus may be based on any of the infectious properties, amplification properties, and cytolytic properties of the virus. Examples of the oncolytic virus include: an animal virus that is infectious and toxic to human cancer cells, but not to normal human cells; a mutant virus that replicates in cancer cells but not in normal cells because the promoter of said viral gene has been substituted with a tumor-specific promoter that is activated only in cancer cells; a mutant animal virus lacking or having mutation in a viral gene that inactivates a cell cycle suppressing gene (e.g. P53, Rb, etc.) to induce cell cycle progression which is essential environment for viral replication, and consequently said mutant animal virus can replicate in cancer cells whose cell cycles are abnormally renewed and progress (regardless of said mutation), but not in normal cells whose cell cycles do not progress; a mutant animal virus which has mutation in a gene important for cell lysis and lyses cancer cells but not normal cells; and an animal virus that has been attenuated by continuous subculture, such as a viral vaccine.

Examples of the viral vector of the present invention include herpes simplex virus, myxoma virus, reovirus, vesicular stomatitis virus, Newcastle disease virus, RS virus, Sendai virus, measles virus, Coxsackie virus, and Seneca Valley virus (Timothy P Cripe et al., Molecular Therapy, 17 (10): 1677-1682). As an example, myxoma virus replicates in cancer cells and causes cell lysis, but it is not infectious to normal human cells. As another example, reovirus is oncolytic in a state isolated from the nature, and is infectious to both cancer cells and cancer stem cells. Vesicular stomatitis virus is not infectious to normal cells because of antiviral interferon response in the acute stage, but is infectious to cancer cells that have been released from such interferon response. Mutant strains or recombinant strains of vesicular stomatitis virus having high oncolytic properties were obtained (Lichty, B D et al., (2004) Trends. Mol. Med. 10: 210-216).

Herein, the term "adenovirus" or "adenoviral vector" means a virus that belongs to genus Mastadenovirus, Adenoviridae and is infectious to mammals. Preferably, it is a human adenovirus. The human adenovirus includes subgenera A to F and serotypes. The adenovirus of the present invention is not particularly limited to specific subgenera and serotypes. For instance, the present adenovirus may be an adenovirus in which a mutation is introduced into E1A and/or E1B. An example of such a mutant E1A protein can be an E1A protein comprising a deletion in the Rb-binding region (E1AΔ24). In addition, an example of a mutant E1B protein can be an E1B protein comprising a deletion in the p53-binding region (E1BΔ55K).

In the present specification, the "desired gene" is not particularly limited, as long as it can be specifically expressed in cancer stem cells and can be then used. For example, when the viral vector of the present invention is used for therapeutic purpose, the desired gene can be a gene encoding a protein essential for replication of virus, or a cytotoxic gene. On the other hand, when the viral vector of the present invention is used for diagnostic or identification purpose, the desired gene can be a marker gene.

In the present specification, the "protein essential for replication of virus" is not particularly limited, as long as it is a protein that plays a role in replication of virus. For example, when an adenovirus is used as the viral vector of the present invention, examples of the protein essential for replication of virus include E1A, E1B, E2, E4, L1, L2, L3, L4 and L5, and among these proteins, preferred proteins are E1A and E1B. Herein, the protein essential for replication of virus may be either a wild-type protein or a mutant protein. An example of a mutant E1A protein can be E1A comprising a deletion in the Rb-binding region (E1AΔ24). In addition, an example of a mutant E1B protein can be E1B comprising a deletion in the p53-binding region (E1BΔ55K). In particular, in the case of the vector of the present invention, replication of adenoviruses is accelerated in cells in which the CD133 promoter is activated. Hence, the replication specificity of the adenovirus in cancer stem cells can be enhanced because the adenoviral vector of the present invention comprises E1AΔ24 and/or E1BΔ55K operably linked to the CD133 promoter.

Moreover, for example, when herpes simplex virus is used as the viral vector of the present invention, examples of the protein essential for replication of virus include ICP34.5 (HSV-1 RL1 gene) and ICP6 ($U_L 31$ gene).

The term "cytotoxic gene" means a gene encoding a substance that induces apoptosis or necrosis to a cell when expressed in the cell, a gene phagocytized by an immunocyte when expressed in the cells or a gene encoding a substance that terminates the growth of a cell when expressed in the cell. The cytotoxic gene may encode a protein or non-coding RNAs such as siRNA and miRNA. The substance encoded by the cytotoxic gene may directly inhibit the survival or growth of a cell. Alternatively, the substance encoded by the cytotoxic gene may cause damage to a cell indirectly, for example, by using with a prodrug, wherein the prodrug is converted into toxic form by said substance. Also, the cytotoxic gene may cause damage or death of the cells or may inhibit the cell growth by being presented on the cell surface to become a target for immunocytes such as cytotoxic T cells or antibodies. Examples of the cytotoxic gene include, but are not limited to: mda-5, mda-7, BAX, PTEN, soluble FGFR, siRNA or antisense against ras, and siRNA or antisense against mda-9; genes that toxify prodrugs, such as HSV-tk (herpes simplex virus-thymidine kinase; which toxifies ganciclovir) and *Escherichia coli* cytosine deaminase (CD; which toxifies 5-fluorocytosine); apoptosis-promoting genes such as p53, adenovirus E3-11.6K (derived from Ad2 and Ad5), adenovirus E3-10.5K, adenovirus E4 genes, and caspase; cell growth-suppressing genes such as p21, a retinoblastoma gene, genes encoding cyclin-dependent kinase inhibitors (p16, p15, p18, p19, etc.), and a growth arrest-specific homeobox (GAX) gene; cytotoxic genes such as Pseudomonas exotoxin; tumor-suppressing genes such as TNF-α, p53, APC, DPC-4, BRCA-1, BRCA-2, WT-1, and MMAC-1; antigenic genes that present antigens recognized by the immune system on the cell surface, such as CEA and p53; cytokine genes such as GM-CSF, interferon α, interferon β, interferon γ, IL-1, IL-2, IL-4, IL-12, IL-10, IL-19 and IL-20; and vascularization-suppressing genes such as angiostatin and siRNA or antisense against VEGF. Further, the cytotoxic gene may also be a gene that enhances reactivity in radiotherapy, chemotherapy or immunotherapy. For example, such a cytotoxic gene may be an EGF receptor (which enhances therapeutic effects obtained by EGFR-specific tyrosine kinase inhibitor such as Gefitinib) or a Her-2 receptor (which enhances therapeutic effects obtained by Herceptin in breast cancer patients). When the toxic gene is a substance that convert a prodrug into toxic form, examples of the gene include a thymidine kinase gene (used in combination with ganciclovir or aciclovir), a cytosine deaminase gene (used in combination with 5-fluorocytosine), an *Escherichia coli*-derived upp gene and a *S. cerevisiae*-derived fur gene (used in combination with 5-fluorouracil), and a thymidine kinase gene or a fusion gene of thymidine kinase and thymidylate kinase (used in combination with azide thymidine).

In the present specification, the term "marker gene" means a gene encoding a substance capable of visualizing a cell, into which the gene is introduced. Examples of a marker gene capable of visualizing a cancer stem cell include: fluorescent proteins such as a green fluorescent protein (GFP) and EGFP (enhanced GFP); and genes encoding β-glucuronidase, β-galactosidase, luciferase or dihydrofolate reductase. Moreover, the present marker gene may also be a marker gene that can be used in image diagnosing, such as a ferritin gene. In the present specification, the expression, cancer stem cells are "labeled," means that the presence or location of cancer stem cells or tissues containing the cancer stem cells is identified temporarily or for a long period of time, depending on utilization purpose, or that cancer stem cells are distinguished from other cells or tissues. Herein, the expression, cancer stem cells are "identified" means to specify the presence or location of cancer stem cells or tissues containing the cancer stem cells temporarily or for a long period of time. Herein, the expression, cancer stem cells are "distinguished" means to distinguish cancer stem cells or tissues containing the cancer stem cells from other cells or other tissues temporarily or for a long period of time. Accordingly, the visualizing of the present invention is not particularly limited as long as it is able to specify the presence or location of cancer stem cells or tissues containing the cancer stem cells, or to distinguish cancer stem cells or tissues containing the cancer stem cells from other cells or other tissues, and it is not necessary that cells other than cancer stem cells are not stained at all. For example, when the presence of cancer stem cells in cancer tissues is distinguished by direct injection of the vector of the present invention into the cancer tissues to stain, it may be sufficient that the cancer stem cells are stained such an extent to be distinguishable from cancer cells other than the cancer stem cells in the cancer tissues, and it is permittable that cancer cells or other cells may be (slightly) stained.

The viral vector of the present invention may also have a transcription unit (hereinafter referred to as a "cancer-specific transcription unit") in which a desired gene is operably linked downstream of a promoter whose activity is enhanced specifically in cancer cells (hereinafter referred to as a "cancer-specific promoter"), as well as a transcription unit (hereinafter referred to as a "CD133 transcription unit") in which a desired gene that is different to or identical to the aforementioned desired gene is operably linked downstream of the CD133 promoter. As a result that the viral vector comprises a combination of the CD133 promoter transcription unit and the cancer-specific transcription unit, the specificity of the toxicity of the viral vector to cancer stem cells can be enhanced, and/or both of toxicity to cancer stem cells and a function of distinguishing or identifying the cancer stem cells can be imparted to a single viral vector. As such a cancer-specific promoter, a promoter whose activity is uniformly enhanced in many types of cancers may be used. Alternatively, a promoter whose expression is enhanced specifically in a target cancer may be used depending on the type of the target cancer. Moreover, the cancer-specific promoter may also be a promoter whose activity is enhanced in cancer stem cells. Examples of the cancer-specific promoter include, but are not limited to, a nestin promoter, a cyclooxygenase-2 (Cox-2) promoter, a multidrug resistance (mdr) protein promoter, a telomerase promoter, a prostate-specific antigen gene promoter, a kallikrein 2 gene promoter, a human a fetoprotein gene promoter, a melanoma differentiation marker tyrosinase promoter, a tyrosinase promoter, a c-erbB-2 gene promoter, a human carcinoembryonic antigen (CEA) gene promoter, a gastrin releasing peptide gene promoter, a human telomerase reverse transcriptase gene promoter, a hexokinase IT gene promoter, an L-plastin gene promoter, a neuron-specific enolase gene promoter, a midkine gene promoter, a human mucin gene MUC 1 promoter, a survivin promoter, an Aurora kinase promoter, and a human mucin gene MUC 4 promoter.

The viral vector of the present invention may further have an additional transcription unit for expression of a desired gene (hereinafter referred to as an "additional transcription unit"). When the viral vector of the present invention has such an additional transcription unit, the promoter that regulates the additional transcription unit is not particularly limited, as long as it is a promoter having activity in a eukaryotic cell (hereinafter referred to as a "eukaryotic cell promoter"). Examples of the promoter that can be used for the additional transcription unit include a Cytomegalovirus promoter (e.g. a Cytomegalovirus immediate-early gene enhancer/promoter), a Rous sarcoma virus long terminal repeat promoter, a human elongation factor 1α promoter, a human ubiquitin c promoter, and a PEG-3 promoter. Inducible promoters such as a mouse breast cancer virus promoter (inducible with dexamethasone) and a tetracycline-reactive or ecdysone-inducible promoter may also be used. Further, a promoter having activity specifically in the above described cancer cells may also be used. Still further, a CD133 promoter may also be used as a promoter that regulates the additional transcription unit.

When the vector of the present invention has a cancer-specific transcription unit and/or an additional transcription unit, the cancer-specific transcription unit and/or the additional transcription unit may be inserted into an adenovirus E1 region, together with a transcription unit in which a CDD133 promoter is operably linked to a nucleic acid encoding a protein essential for replication of virus in the viral genome, or they may also be inserted into other regions (e.g. E3 region) of the adenovirus.

When the vector of the present invention has the cancer-specific transcription unit and/or the additional transcription unit, a gene encoding a protein essential for replication of virus, a marker gene, or a cytotoxic gene can be used as a desired gene.

Furthermore, the vector of the present invention may also be a multifactorial cancer-specific replication-controlled recombinant adenoviral system (m-CRA; Japanese Patent Laid-Open No. 2005-046101 and International Publication No. WO 2005/012536).

Examples of the adenoviral vector of the present invention include the following adenoviral vectors: (a) an adenoviral vector having the following transcription units:

(a1) a CD133 transcription unit consisting of a CD133 promoter and an E1A gene or E1AΔ24 gene operably linked downstream of said promoter, (a2) a transcription unit consisting of a eukaryotic cell promoter, a cancer-specific promoter or CD133 promoter, and an E1B gene or E1BΔ55K gene operably linked downstream of said promoter, or a transcription unit consisting of an E1BΔ19K gene operably linked downstream of a cancer-specific promoter, and (a3) optionally, an additional transcription unit consisting of a eukaryotic cell promoter, a cancer-specific promoter or CD133 promoter, and a marker gene or cytotoxic gene operably linked downstream of said promoter;

(b) an adenoviral vector having the following transcription units:

(b1) a transcription unit consisting of a eukaryotic cell promoter, a cancer-specific promoter or CD133 promoter, and an E1A gene or E1AΔ24 gene operably linked downstream of said promoter, (b2) a CD133 transcription unit consisting of a CD133 promoter and a E1B gene or E1BΔ55K gene operably linked downstream of said CD133 promoter, and (b3) optionally, an additional transcription unit consisting of a eukaryotic cell promoter, a cancer-specific promoter or CD133 promoter, and a marker gene or cytotoxic gene operably linked downstream of said promoter; and (c) an adenoviral vector having the following transcription units:

(c1) a transcription unit consisting of a eukaryotic cell promoter, a cancer-specific promoter or CD133 promoter, and an E1A gene or E1AΔ24 gene operably linked downstream of said promoter, (c2) a transcription unit consisting of a eukaryotic cell promoter, a cancer-specific promoter or CD133 promoter, and an E1B gene or E1BΔ55K gene operably linked downstream of said promoter, and (c3) a CD133 transcription unit consisting of a CD133 promoter and a marker gene or cytotoxic gene operably linked downstream of said CD133 promoter. viral vectorviral vectorviral vector CD133-CRA means a conditionally replicating adenoviral vector (CRA) in which a CD133 promoter is operably linked to a nucleic acid encoding protein which is essential for replication of virus (e.g. E1A and E1B) in the viral genome. CD133-CRA is the same as the adenoviral vector described in (a) and (b) above.

Further, the viral vector of the present invention may be enhanced its infection specificity to cancer stem cells by modification or substitution of virus fiber or hexon. For instance, a ligand against a surface protein of the cancer stem cell may be embedded into the HI loop of a viral fiber or in a capsid such as a hexon protein or the like.

Since the vector of the present invention is able to visualize or cause damage specifically to cancer stem cells, it can be used as a pharmaceutical composition for diagnosing, preventing and treating cancer, and inhibiting cancer metastasis, or as a pharmaceutical composition for visualizing, causing damage to, and killing cancer stem cells. Examples of cancer that can be diagnosed, prevented and treated, or the metastasis of which can be suppressed by the vector of the present invention or a pharmaceutical composition containing the same, include brain tumor, glioblastoma, head and neck cancer, stomach cancer, lung cancer, breast cancer, uterine cancer, ovarian cancer, hepatic cancer, bronchial cancer, epipharynx carcinoma, pharyngeal cancer, esophageal cancer, bladder cancer, pancreatic cancer, prostate cancer, colon cancer, osteosarcoma, skin cancer, melanoma, thyroid cancer, parathyroid cancer, ureteral cancer, cervical cancer, and malignant tumors formed in hemopoietic organs or blood (e.g. leukemia, malignant lymphoma, etc.). Preferably, they are cancers, in which the presence of cancer stem cells has been confirmed. Examples of such cancers include brain tumor, glioblastoma, head and neck cancer, stomach cancer, lung cancer, breast cancer, hepatic cancer, bladder cancer, colon cancer, melanoma, pancreatic cancer, prostate cancer, and ovarian cancer (S. Bomken et al., British Journal of cancer (2010) 103: 439-445; Natasha Y. Frank et al., The Journal of Clinical Investigation (2010) 120: 41-50). Particularly preferably, they are cancers, in which the expression of CD133 in the cancer stem cells has been confirmed. Examples of such cancers include brain tumor, breast cancer, prostate cancer, pancreatic cancer, lung cancer, hepatic cancer, colon cancer, melanoma, and prostate cancer (Tabu et al., Molecular Cancer (2010) 9: 39; Abe et al., Cell Technology, (2008) 27 (10) 1036-1041). The vector of the present invention or a pharmaceutical composition containing the same may be used as an agent for identifying, distinguishing, visualizing, causing damage to or killing cancer stem cells in the above described cancers.

In the present specification, the expression, "cause damage" (to cancer stem cells) means to make cancer stem cells to a state not being enable to exhibit their functions. It specifically means to make cancer stem cells to a state in which they cannot autonomously proliferate and/or differentiate into cancer cells. The expression "cause damage specifically to cancer stem cells" means that such damage is given to cancer stem cells more strongly than to normal cells, and it does not mean that there is no toxicity to normal cells or to cancer cells other than cancer stem cells. In addition, the term "cause damage" includes destruction of cancer stem cells (including metastatic cancer stem cells) by an immune system in a subject, and inhibition of the growth of said cancer stem cells, and/or inhibition of the differentiation of said cancer stem cells, as well as destruction of said cancer stem cells by apoptosis or necrosis. Alternatively, such damage may be given to cancer stem cells as a result of cell (in particular, cancer stem cell) lysis caused by the viral vector of the present invention which can replicate specifically in cancer stem cells and having cytolytic (or oncolytic) properties after replication of the vector in the cells. In other ways, a cytotoxic gene may give damage to cancer stem cells by expressing in cells so as to induce apoptosis or necrosis to the cells, or by converting a co-employed prodrug into toxic form, or by being presented on the cell surface so that it is targeted by an immunocyte or antibody. In the present specification, the term "agent for causing damage" means an agent that causes such damage to cancer stem cells. The present invention includes an agent for causing damage to cancer stem cells, comprising the viral vector of the present invention as an active ingredient.

In the present specification, the term "cancer stem cells" means cells in cancer tissues that can differentiate to produce a large number of cancer cells around themselves, while maintaining themselves by self-replication. Since a small number of cancer stem cells differentiate and generate a large number of cancer cells that form cancer tissues, the cancer stem cells are also referred to as cancer-initiating cells or initiating cells of tumor or cancer.

In the present specification, the term "cancer stem cells" means cells which exist in tumor and have a self-replicating ability and an ability to provide heterogeneous lineages of cancer cells including tumor (Clarke M F et al., Cancer Res. (2006) 66: 9339-9344). That is to say, cancer stem cells have both an ability to generate daughter cells having the same properties as themselves and an ability to differentiate into cells forming cancer tissues (in particular, malignant tumor). However, this means that cancer stem cells have the stem-like properties to a certain extent, and that the cancer stem cells do not need to have (and are not limited to) the rigid properties of stem cells, such as those of normal stem cells. It is rather important that cancer stem cells are a main cause of the malignant alteration of cancer. Because a small number of cancer stem cells can differentiate and generate a large number of cancer cells that form cancer tissues, the cancer stem cells are also referred to as Tumor-Initiating Cells or Cancer Initiating Cells (cancer-initiating cells, or initiating cells of tumor or cancer). The cancer stem cells of the present invention include these cancer-initiating cells, or initiating cells of tumor or cancer (Neuzil J, et al. Biochem Biophys Res Comm. 355; 855-859, 2007). For instance, such cancer stem cells may be cells that form a cancer in an immunodeficient mouse, when the cells are transplanted in an amount of several to several tens of thousands of cells (preferably, several tens of to several thousands of cells) into the immunodeficient mouse. Moreover, it has been known that cancer stem cells express markers such as CD24, CD44, CD90, CD133 or ABCB5 in a solid cancer, although the cancer stem cells described in the present specification are not limited thereto. Examples of the cancer stem cells of the present invention include cancer stem cells in solid cancers and sarcomas, such as brain tumor, glioblastoma, head and neck cancer, stomach cancer, lung cancer, breast cancer, uterine cancer, ovarian cancer, hepatic cancer, bronchial cancer, epipharynx carcinoma, pharyngeal cancer, esophageal cancer, bladder cancer, pancreatic cancer, prostate cancer, colon cancer, osteosarcoma, skin cancer, melanoma, thyroid cancer, parathyroid cancer, ureteral cancer and cervical cancer, and malignant tumors formed in hemopoietic organs or blood (e.g. leukemia such as acute lymphatic leukemia, malignant lymphoma, etc.) Preferably, the cancer stem cells are brain tumor stem cells or glioblastoma stem cells.

Advantageous Effects of Invention

The viral vector of the present invention can express a desired gene specifically in cancer stem cells. In addition, by employing a replicative virus that induces viral replication specific in cancer stem cells as the viral vector of the present invention, oncolytic (cancer stem cell-lytic) therapeutic effects can be obtained. Moreover, loading a marker gene or a therapeutic gene in the viral vector of the present invention allows cancer stem cells to be visualized or to be induced or enhanced therapeutic effects after the viral infection. Accordingly, the oncolytic viral vector of the present invention loading a marker gene or a therapeutic gene can damage cancer stem cells as a target that is responsible for treatment resistance by the oncolytic effects of the virus or by the therapeutic gene, and at the same time, can visualize the presence of the cancer stem cells. As such, the viral vector of the present invention can be used for evaluation of the therapeutic effects on a cancer by using the presence of cancer stem cells as an indicator, and can also be used as an indicator when such cancer stem cells are surgically excised. Furthermore, the viral vector of the present invention itself can be targeted to and used to treat cancer stem cells. For now, there has been no technique which can specifically identify cancer stem cells or specifically treat cancer stem cells, not only in using viral vectors. Hence, therapeutic agents and therapeutic techniques that are effective for cancer stem cells can be efficiently developed by using the viral vector of the present invention which can selectively identify cancer stem cells. Further, the viral vector of the present invention can represent, visualize and/or identify cancer stem cells in the body of a cancer patient which have a high infiltration/metastatic ability and is a main cause of malignant alteration during the diagnosis or before the treatment of the cancer patient, which figure out a ratio or location of such cancer stem cells and provide a revolutionary method of determining the prognosis of a cancer patient or a revolutionary way to select a treatment site or a therapeutic method. Further, cancer stem cells are resistant to existing therapeutic methods such as anticancer agents or radiation. The remaining cancer stem cells after completion of the treatment lead to the recurrence of cancer, and thus, such remaining cancer stem cells are considered to be a main cause of determining the poor prognosis and lethality of the patient. Accordingly, using the viral vector of the present invention, cancer stem cells in the body of a cancer patient are identified, visualized, and/or detected in the patient's body after completion of the treatment, so as to establish a revolutionary technique of evaluating the effectiveness of a therapeutic method on the cancer patient or a revolutionary diagnostic and/or therapeutic method that copes with cancer recurrence after completion of the treatment, or so as to monitor the remaining cancer stem cells after completion of the treatment. Thus, the viral vector of the present invention capable of selectively diagnosing and/or treating cancer stem cells enables the diagnosis of malignant alteration of cancer and the treatment of cells causing such malignant alteration of cancer. As a result, because of the viral vector of the present invention, a large number of totally new methods for diagnosing and/or treating cancer patients are produced, as described above, and thus, the present viral vector greatly improves the diagnosis and treatment of cancer. Therefore, the viral vector of the present invention can be used for diagnoses and treatments that target various cancer stem cells, and the radical cure of refractory cancer in clinical sites and prevention of the recurrence thereof can be realized.

DESCRIPTION OF EMBODIMENTS

1. Method for Producing Viral Vector

Figure 1:
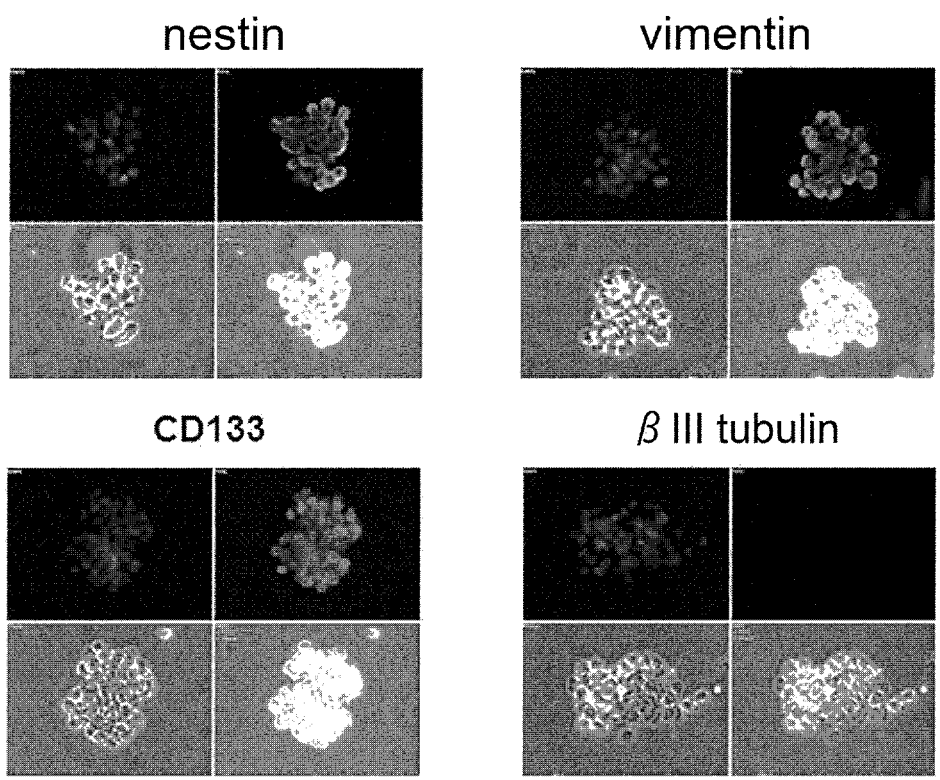
FIG. 1 shows the results obtained by confirming the expression of nestin, vimentin, CD133 and βIII tubulin (Tuj1) in human nerve cancer stem cells (which are human glioblastoma stem cells: the same applies below) X01GBS by performing immunostaining on the cells. In each photograph in the figure, the upper left view shows a blue dye indicating DAPI, the upper right view shows green dyes indicating nestin, vimentin, CD133 and βIII tubulin, respectively. In addition, the lower left view shows a microphotograph, and the lower right view shows a photograph formed by synthesizing all of the three other photographs.

The viral vector of the present invention can be produced by appropriately adopting well known methods for producing a viral vector by a person skilled in the art. For example, the viral vector can be produced by recombination of a viral backbone plasmid having a copy of almost complete viral genome with a shuttle vector plasmid having a CD133 transcription unit according to gene recombination technology. Such gene recombination can be carried out by homologous recombination, recombination utilizing restriction sites (preferably, special restriction sites such as I-CeuI and PI-SceI), or recombination utilizing a recombination reaction (e.g. Cre-LoxP).

When the viral vector of the present invention is adenovirus, it can be produced, for example, by recombination of an adenoviral backbone plasmid having a copy of almost complete adenoviral genome which lack the E1 gene with a shuttle vector plasmid having a CD133 transcription unit.

When the viral vector of the present invention has a cancer-specific transcription unit and/or an additional transcription unit, the viral vector may be produced by recombination of a single shuttle vector plasmid having a CD133 transcription unit, a cancer-specific transcription unit and/or an additional transcription unit, with a viral backbone plasmid. Alternatively, it may also be produced by using a shuttle vector plasmid having a CD133 transcription unit and a different shuttle vector plasmid having a cancer-specific transcription unit and/or an additional transcription unit, and recombining them with an adenoviral backbone plasmid, separately or simultaneously. When such a cancer-specific transcription unit and/or an additional transcription unit are incorporated into a region other than the E1 region of an adenovirus (the E3 region, etc.), it is desired to use a separate shuttle vector plasmid for said units from a shuttle vector plasmid having a CD133 transcription unit and to recombine the shuttle vector plasmids with the adenoviral backbone plasmid, separately.

When the viral vector of the present invention has a modification or substitution of virus fiber or hexon, the modified or substituted vector can be produced by a method well known to a person skilled in the art. For example, when the viral vector of the present invention is an adenovirus, such a modified or substituted viral vector can be produced in accordance with the methods described in Krasnykh et al, Cancer Res (2000) 60 (24): 6784-6787, Ruigork et al., J. Mol. Biol. (1990) 215: 589-596, Krasnyk et al., J. Virol. (1996) 70: 6839-6846, Henry et al., J. Virol. (1994) 68 (6): 5239-6846, and International Publication No. WO 00/67576.

2. Therapeutic Method

The present invention relates to a therapeutic method, preventive method or metastasis-suppressing method for cancer, comprising administering to a patient in need thereof, a viral vector having a CD133 promoter operably linked to a gene encoding a protein essential for replication of virus, wherein the viral vector is a viral vector which can replicate specifically in cancer stem cells, and/or a viral vector having a cytotoxic gene (which are hereinafter collectively referred to as a "therapeutic viral vector), which are included in the viral vectors of the present invention. Since the therapeutic viral vector of the present invention can damage cancer stem cells which are responsible for generation of cancer cells, such a viral vector can be administered to a cancer patient or a patient predicted to be affected by cancer to treat or prevent cancer or to suppress metastasis of the cancer. Accordingly, an example of the present invention is a therapeutic method, preventive method, or metastasis-suppressing method for cancer, comprising administering a therapeutic viral vector to a patient in need thereof, and allowing the viral vector to replicate in the cancer stem cells in the patient or allowing a cytotoxic gene to be expressed in the patient.

Administration of the therapeutic viral vector of the present invention can be appropriately selected depending on therapeutic target disease, age, sex, administration route, intended purpose, etc. For example, the present therapeutic viral vector can be administered at a titer of $1\times10^5$ to $1\times10^{12}$ pfu. As an administration method, intratumoral infusion, intravascular (intravenous or intra-arterial) injection, intrameningeal injection, intramuscular injection, intracutaneous injection, subcutaneous injection, transmucosal administration (through the mucosa of lung, etc.), transnasal administration and the like can be applied. For example, the vector of the present invention can be administered at a titer of $1\times10^{10}$ pfu once every three days for 5 days.

Moreover, the therapeutic viral vector of the present invention may be used in combination with other anticancer therapy. Since the therapeutic viral vector of the present invention targets and treats cancer stem cells, combined anticancer therapies include chemotherapy, radiotherapy, immunotherapy, and surgical treatment. Examples of an anticancer agent used in such combined treatment include taxol derivatives such as cisplatin, adriamycin, doxorubicin, and paclitaxel. Furthermore, when the therapeutic viral vector of the present invention has a cytotoxic gene that toxifies a prodrug, an appropriate prodrug is used in combination. Examples of such a prodrug include ganciclovir or aciclovir (thymidine kinase gene), 5-fluorocytosine (cytosine deaminase gene), 5-fluorouracil (*Escherichia coli*-derived upp gene and *S. cerevisiae*-derived fur gene), and azidothymidine (thymidine kinase gene, or fusion gene of thymidine kinase and thymidylate kinase) (wherein the gene in each parentheses indicates a cytotoxic gene to be combined).

Furthermore, since the therapeutic viral vector can damage specifically cancer stem cells, it can be used in a method for damaging cancer stem cells. Accordingly, the present invention includes a method for producing damage to cancer stem cells, comprising a step of administering a therapeutic viral vector to a subject in need thereof. An example of the present invention is a method for producing damage to cancer stem cells, comprising administering a therapeutic viral vector to a patient in need thereof, and allowing the viral vector to replicate in the cancer stem cells in said patient or allowing a cytotoxic gene to be expressed in said patient. The method for producing damage to cancer stem cells of the present invention can be specifically carried out in accordance with the above described therapeutic method and/or preventive method of the present invention for cancer.

3. Diagnostic and/or Visualizing Methods

The present invention relates to a method for diagnosing cancer or a method for visualizing cancer stem cells, each of which comprises administering a viral vector having a marker gene (hereinafter referred to as a "visualizing viral vector"), which are included in the viral vectors of the present invention, to a target patient. Since the visualizing viral vector of the present invention can express a marker gene specifically in cancer stem cells, the cancer stem cells can be identified or distinguished by administering such a viral vector to a cancer patient or a patient predicted to be affected by cancer. Since cancer stem cells have been known to be present at a percentage of several to dozen percent in cancer cells, cancer can be diagnosed using the presence of cancer stem cells as an indicator. In addition, in excision of cancer or the like, it is considered important to eliminate cancer stem cells that are the root of proliferation of the cancer. Specific visualization of the cancer stem cells can increase the success rate of operation by supporting secure elimination of cancer stem cells, and thus improve the prognosis of a patient after cthe operation. Specifically, the present invention relates to a method for diagnosing cancer or a method for visualizing cancer stem cells, each of which comprises administering a visualizing viral vector to a target patient and detecting an expression product of the marker gene. Detection of the expression product of the marker gene can be appropriately selected depending on the type of a marker gene used and intended purpose. For example, a dye or a fluorochrome may be confirmed by visual observation during a surgical operation, or it may also be detected by image diagnosing. Moreover, the diagnosis of cancer or the visualizing of cancer stem cells may be carried out by visualization of the cancer stem cells, or it may also be carried out by detectable means other than visual means. For example, the method for diagnosing cancer or method for visualizing cancer stem cells of the present invention may be a method for visualizing cancer stem cells, comprising administering a visualizing viral vector to a target patient.

Administration of the visualizing viral vector of the present invention can be carried out by administering the viral vector of the present invention to a patient in accordance with the above described therapeutic method or preventive method of the present invention for cancer.

4. Pharmaceutical Composition

A pharmaceutical composition comprising the viral vector of the present invention as an active ingredient (which includes a therapeutic agent, a preventive agent, a metastasis-suppressing agent and a diagnostic agent for cancer, and an agent for visualizing cancer stem cells and an agent for causing damage) may be a composition comprising one or more pharmaceutically acceptable carriers as well as the active ingredient. When the pharmaceutical composition is a liquid agent, such pharmaceutically acceptable carrier(s) may be generally known carrier(s) that can be sterilized and administered to a human. Examples of such a carrier include, but are not limited to, a physiological saline, sterilized water, a Ringer's injection, a buffered saline, an albumin injection, a dextrose solution, a maltodextrin solution, glycerol, ethanol, and a combination thereof. Also, the pharmaceutical composition may further comprise an antioxidant, a buffer and a bacteriostatic agent, as necessary. Moreover, the pharmaceutical composition may be an agent for injection, which can be prepared when used. In this case, the pharmaceutical composition (pharmaceutical composition kit) may comprise a diluent, a dispersant, a surfactant, a binder, and a lubricant.

EXAMPLES

Hereinafter, the present invention will be more specifically described in the following examples. However, these examples are not intended to limit the scope of the present invention. All publications cited throughout the present application are incorporated herein by reference in their entirety.

(Example 1) Confirmation of the Cancer Stem Cell Properties of Human Glioblastoma Stem Cells and the Expression of a Cancer Stem Cell Surface Marker CD133 by Performing Immunostaining on the Cells (1) Cells Human glioblastoma stem cells described in Soeda A, et al., J Biol Chem 2008; 283; 10958-66 were used herein. X01GBS cells are a fraction of cancer stem cells in X01 GB cells, and are a group of cells prepared by "concentration" of a cancer stem cell fraction using a medium under undifferentiation conditions according to a Sphere culture method. Thus, unless otherwise specified, hereinafter, the term "human glioblastoma stem cells (X01GBS)" means human glioblastoma stem cells (or X01 GB-CSC) described in Soeda A, et al., J Biol Chem 2008; 283; 10958-66. As culture conditions, glioblastoma stem cells (X01GBS) were cultured at 5% $CO_2$, 37° C. in a Dulbecco's modified Eagle's medium/F-12 (D6421, Sigma) medium containing B-27 (Invitrogen), 10% FBS, to which recombinant human FGF-2 (20 ng/ml; R & D Systems, Minneapolis, Minn.) and recombinant human EGF (20 ng/ml; R & D Systems) had been added, penicillin G, and streptomycin sulfate. Unless otherwise specified, the X01GBS cells were cultured under the same conditions as described above in the following experiments.

On the other hand, X01GBD cells were a cell group that were produced by concentration of the "differentiated human glioblastoma cells" (differentiated human glioblastoma) established from the X01GBS cells that were a cell group prepared by concentration of the human glioblastoma stem cells (glioblastoma-derived cancer stem cells) by the following method. The X01GBD cells were established and maintained by the cell-establishing method described in Inagaki A, et al. Biochem Biopys Res Commun 2007; 361; 586-592 and a maintenance culture method in which cells are maintained in a differentiated state. That is to say, the X01GBS cells were subjected to an adhesive monolayer culture in a Dulbecco's modified Eagle's medium/F-12 medium, to which 10% fetal bovine serum had been added and from which FGF-2 had been removed, using a general adhesive culture dish. The cells were cultured and maintained for a long period of time (wherein 50 or more subcultures were repeated), so as to obtain X01GBD cells as a cell group, in which cancer stem cell fractions were significantly reduced and a majority of them was replaced with differentiated cancer cell fractions. The characteristics of the X01GBD cells were as described in Inagaki A, et al., Biochem Biopys Res Commun 2007; 361; 586-592.

Thus, a X01GBS cell group of highly undifferentiated cancer stem cell fractions having high malignancy and a X01GBD cell group of differentiated cells having low malignancy were established from the same tissue from the same patient, i.e. human glioblastoma.

(2) Primary Antibody

As primary antibodies, the following antibodies were used:

an anti-nestin rabbit polyclonal antibody (Chemicon, Temecula, Calif.), an anti-vimentin rabbit polyclonal antibody (Ab45939, Abcam, UK), an anti-CD133 rabbit polyclonal antibody (Ab19898, Abcam, UK), and an anti-βIII tubulin (Tuj1) mouse monoclonal antibody TU20 (Ab7751, Abcam, UK).

(3) Secondary Antibody

As a secondary antibody, the following antibody binding to a green fluorochrome with a wavelength of 488 nm was used:

Alexa fluorophore-conjugated 488 (mouse/rabbit, Molecular Probes, Invitrogen).

(4) Immunostaining on Cells

Cell masses (spheres) of human glioblastoma stem cells (X01GBS) were disseminated on a cover glass coated with 0.1% gelatin, and they were then cultured at 5% $CO_2$ at 37° C. for 4 hours in a Dulbecco's modified Eagle's medium/F-12 (D6421, Sigma) medium containing B-27 (Invitrogen), 10% FBS, to which recombinant human FGF-2 (20 ng/ml; R & D Systems, Minneapolis, Minn.) and recombinant human EGF (20 ng/ml; R & D Systems) had been added, penicillin G, and streptomycin sulfate. Thereafter, the cultured cells were washed with 1×PBS, and were then immobilized with 400 μL of 4% PFA/PBS at a room temperature for 15 minutes. The thus immobilized cells were washed with 1×PBS, and the primary antibody was added to the cells, so that they were allowed to react at a room temperature for 1 hour. After completion of the reaction, the resultant was washed with 1×PBS, and the secondary antibody was then added thereto to the above described dilution rate. The obtained mixture was reacted at a room temperature for 30 minutes, and was then washed with PBS.

(5) DAPI Staining

Cell nuclei were immediately stained by adding a droplet of Mounting Medium with DAPI (H-1500, Vector laboratories, Inc., USA) to the cells that had been immunostained at a room temperature.

After completion of the staining, the cell fluorescence image was taken on an inverted fluorescence microscope Axio Observer. A1 (Carl Zeiss) equipped with a filter set suitable for detection of FITC or DAPI. The observation results are shown in FIG. 1. In each figure, the upper right view shows cancer stem cells and the protein expression of a nerve cell marker (the name of which is described on the view) detected by FITC; the upper left view is a photograph showing the nucleus detected by DAPI; the lower left view is a photograph showing a phase-contrast image (no fluorescence); and the lower right view is a photograph of an image merged by overlapping these three types of photographs. Nestin is an intermediate filament of class VI, and it is one of the important markers for neural stem cells that have been reported to be strongly expressed in neural stem cells in the midbrain. Vimentin is a mesenchymal cell marker that has been reported to be expressed only during the development. βIII tubulin (Tuj1) has been reported to be a protein that forms the structure of nerve cells. Since the gene expression of βIII tubulin is mainly found in nerve cells, it is used as a marker for nerve cells. In addition, DAPI is a fluorochrome for staining the nucleus to blue. As shown in FIG. 1, the human glioblastoma stem cells (X01GBS) used in the present experiment were stained with antibodies against the neural stem cell marker nestin, and vimentin, but were not stained with an antibody against the mature nerve cell marker pill tubulin. As a result, it was found that the human glioblastoma stem cells (X01GBS) have the properties of stem cells. Moreover, the human glioblastoma stem cells (X01GBS) used in the present experiment were stained with an antibody against CD133. As a result, it was confirmed that these cells express CD133.

(Example 2) Confirmation by Western Blotting of Expression of Cancer Stem Cell Surface Marker CD133 on Human Glioblastoma Stem Cells (X01GBS)

(1) Cells

Human glioblastoma stem cells (X01GBS), and as positive controls, colon cancer cells (Caco-2) and human iPS cells (201B7, purchased from RIKEN), were used.

(2) Antibodies

An anti-CD133 rabbit polyclonal antibody (Ab19898, Abcam, UK) was used as a primary antibody (dilution rate 1:1000), and a goat anti-rabbit polyclonal antibody IgG/HRP (Dako, Cytomation) (dilution rate 1:2000) was used as a secondary antibody.

(3) Western Blotting

A culture solution in a 10-cm dish containing the cultured cells was discarded, and the dish was then washed with PBS. Thereafter, 1 mL of a cell lysis RIPA buffer (0.5% NP40, 0.1% SDS, 0.5% sodium deoxycholate, 150 mM NaCl, and 50 mM Tris (pH7.5)), which contained a 0.5 mM protein protective agent PMSF and Protease inhibitor cocktail (which was added immediately before the reaction), was added, so as to lyse the cells. Thereafter, a 2× sample buffer (4% SDS, 20% glycerol, 0.06% β-mercaptoethanol, 100 mM Tris (pH6.8), and 0.1% bromophenol blue) was added in an amount equal to the cell lysis solution to the resulting cells, and the obtained mixture was then boiled at 95° C. for 5 minutes. 20 μg of the sample was applied onto 10% polyacrylamide gel (196-12921, Wako), followed by performing electrophoresis. The membrane was removed from a transcription apparatus, and it was then immersed in a blocking buffer (5% non-fat dry milk, 10 mM Tris (pH7.5), 100 mM NaCl, and 0.1% Tween20), followed by shaking at a room temperature for 1 hour for blocking. Thereafter, the blocking buffer was removed, and the primary antibody reaction solution diluted with a blocking buffer to a dilution ratio of 1:1000 was then added. The membrane was shaken at a room temperature for 1 hour for reaction. Thereafter, the primary antibody solution was removed, and a wash buffer (10 mM Tris (pH7.5), 100 mM NaCl, and 0.1% Tween20) was then added, and the membrane was washed at a room temperature for 15 minutes three times, while shaking the membrane. The wash buffer was removed, and the secondary antibody solution diluted by a factor of 2000 was added, and the membrane was shaken at a room temperature for 1 hour for reaction. Subsequently, the secondary antibody reaction solution was removed, and a wash buffer was added, and the membrane was washed at a room temperature for 15 minutes three times, while shaking the membrane. After the removal of the wash buffer, a 0.125 mL/cm² chemiluminescence reaction solution Chemi-Lumi One (05027-20, Wako) was added to the membrane, and they were reacted for 1 minute, and the membrane was then exposed to light to detect the expression of the protein.

Figure 2:
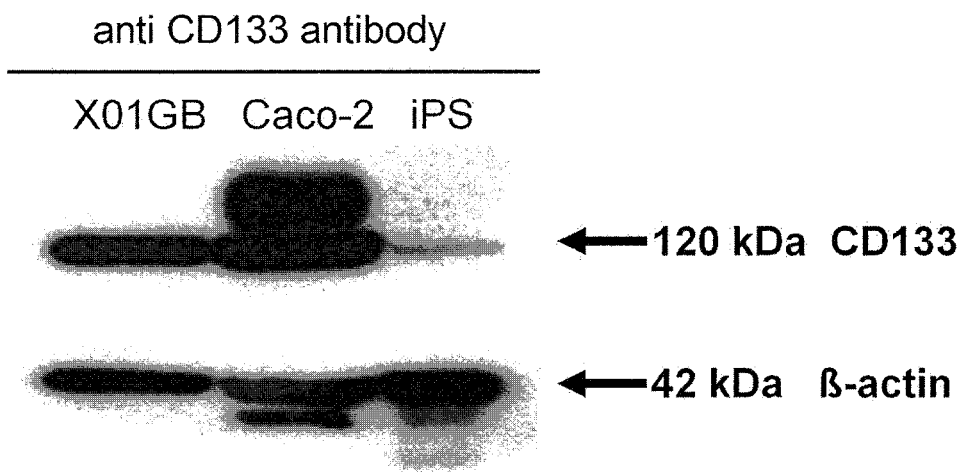
FIG. 2 shows the results obtained by confirming the expression of CD133 in human glioblastoma stem cells (X01GBS), colon carcinoma cells (Caco-2), and human iPS cells by performing Western blotting on the cells. The term "120 kDa CD133" indicates CD133, whereas the term "42 kDa β-actin" indicates β-actin as a control.

The results are shown in FIG. 2. As a result of the Western blotting, the expression of CD133 was confirmed in Caco-2 cells and human iPS cells used as positive controls. In addition, the expression of CD133 was confirmed also in the X01GBS cells used in the present experiment by the Western blotting.

(Example 3) Confirmation by Flow Cytometry (FCM) of the Number of CD133(+) Cells (1) FCM ($1^{st}$ Time)

FCM analysis was carried out in accordance with protocols associated with the antibody used in the analysis, produced by the manufacturer Miltenyi Biotec. When human glioblastoma stem cells (X01GBS) were used, the content of CD133(+) cells was determined.

In the figure, cells contained in the range enclosed with an ellipse were defined as total cells, and were subjected to the analysis.

(2) FCM ($2^{nd}$ Time)

FACS was carried out in the same manner as in the $1^{st}$ FCM. A mouse anti-human CD133/2 (293C3)-PE and mouse IgG-PE (both of which were manufactured by Miltenyi Biotec) were used as antibodies. Detection was carried out using BD FACSAria™ II Flow Cytometer.

Figure 3:
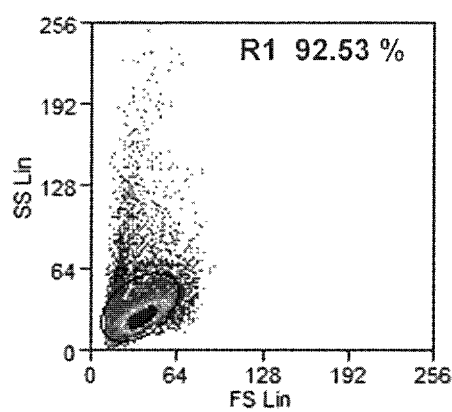
FIG. 3 shows the results obtained by measuring the content of CD133(+) cells in human glioblastoma stem cells (X01GBS) by flow cytometry. The left view shows a total cell population subjected to flow cytometry, and in the view, the horizontal axis (FS Lin) indicates forward scatter (FS), which refects the size of cells, whereas the longitudinal axis (SS Lin) indicates side scatter (SS), which refects cell morphology, or internal cell structure such as a nucleus and a granule. The numerical value (%) in the left view indicates the ratio of the number of cells contained in the cell population enclosed with the ellipse R1 to the total cell number. The right view indicates the content of CD133(+) cells in the cell population R1. In the same view, the horizontal axis (PE Log) indicates the content of CD133(+) cells, whereas the longitudinal axis (FITC Log) has no particular meanings. The numerical value in the right view (CD133(+) 20.18%) indicates the ratio of CD133(+) cells in the cell population R1.
Figure 3:
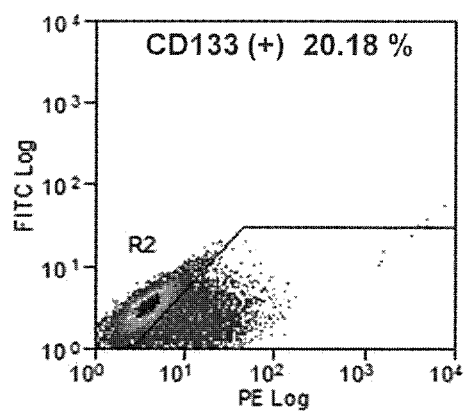

From among a plurality of experiments performed, representative results are shown in FIG. 3. In the figure, the horizontal axis (PE Log) indicates CD133(+) cells as logarithmic values, and the longitudinal axis (FITC Log) has no particular meanings. As a result of the analysis by flow cytometry, the percentage of the CD133(+) cells to the total cell number of X01GBS was approximately 10% to 20.18%. From these results, it was demonstrated that approximately 10% to 20% of human glioblastoma stem cells (X01GBS) express CD133 on the cell surface.

(Example 4) Analysis by Flow Cytometry of the Expression of CD133 in X01GBS Cells and X01GBD Cells X01GBS cells as a concentrated fraction of human glioblastoma stem cells and X01GBD cells as a concentrated fraction of cancer cells differentiated from the X01GBS cells were simultaneously subjected to flow cytometry, together with Caco-2 cells (colon cancer) as a CD133 expression-positive cell line and normal WI-38 cells (fibroblasts) as CD133 expression-negative cells.

Figure 4:
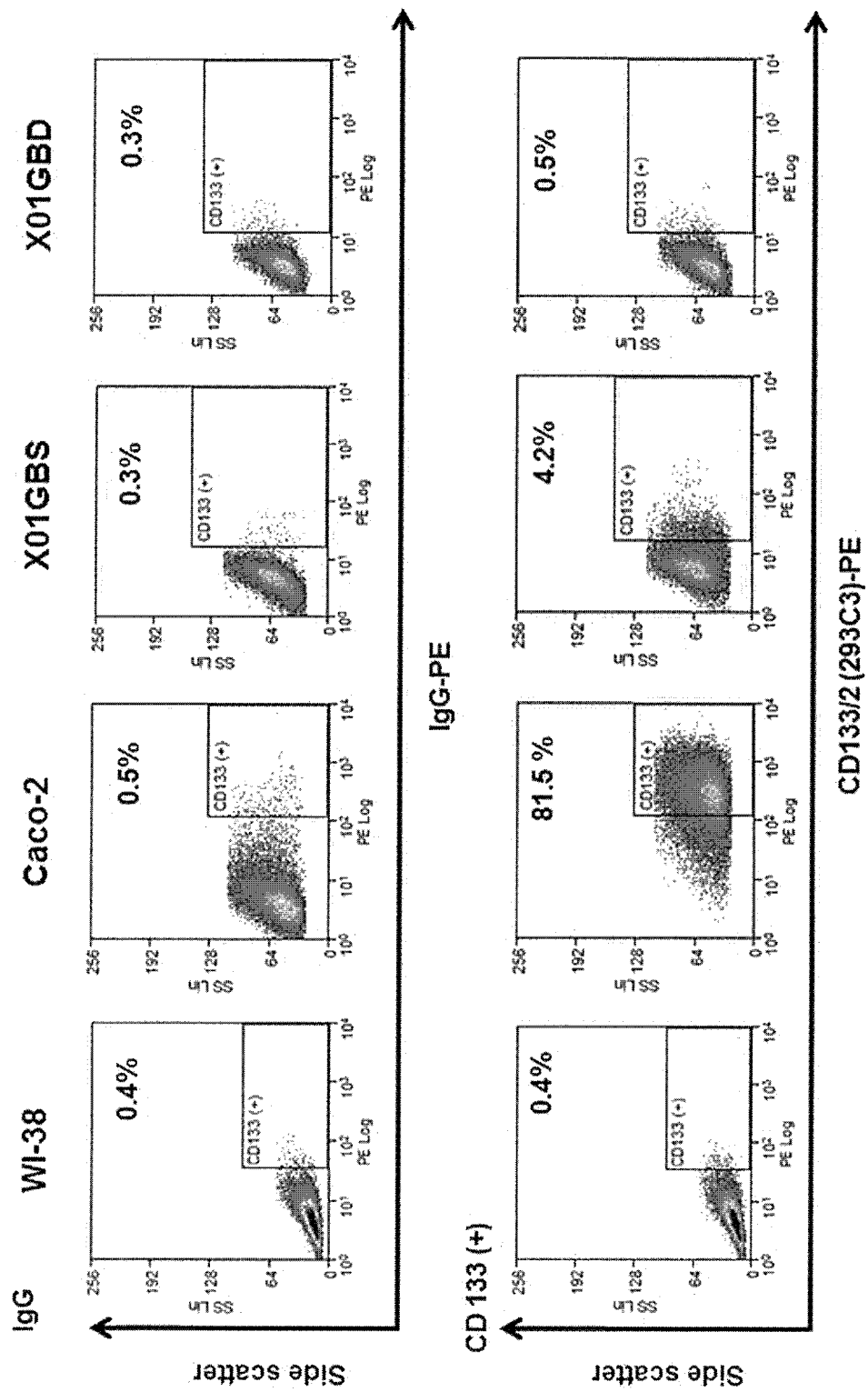
FIG. 4 shows the results obtained by measuring by flow cytometry, the expression of CD133 in normal cells WI-38 (fibroblast) that are CD133-negative cells, Caco-2 (colon cancer) that is a cell line positive to CD133 expression, X01GBS, and X01GBD. The upper case indicates the results obtained using an IgG antibody as a negative control, whereas the lower case indicates the results obtained using an anti-CD133 antibody. The longitudinal axis (Side Scatter) indicates data obtained with side scatter, which reflects cell morphology, or internal cell structure such as a nucleus and a granule. The numerical value (%) in the view indicates the ratio of the number of cells contained in a cell population enclosed with the square to the total cell number.

From among a plurality of experiments performed, representative results are shown in FIG. 4. The graphs in the upper case show the results of flow cytometry for evaluating the properties of an antibody, in which an IgG antibody was used as a negative control, whereas the graphs in the lower case show the results of flow cytometry in which an anti-CD133 antibody was used. In comparison with the X01GBS cells, 4.2% of which were CD133-positive, only 0.5% of the X01GBD cells were CD133-positive. Accordingly, it became clear that CD133-positive cells were concentrated in the X01GBS cells. In addition, there was a slight difference between FIG. 3 and FIG. 4 in terms of the ratio of CD133-positive cells in the X01GBS cells. It was considered that this was caused by slight differences in experimental conditions (a method of performing fluorescence correction among target cells using a flow cytometer, a difference in the longitudinal axis/side population was determined in FIG. 4, etc.), slight differences in cell states in every experiments, etc.

(Example 5) Analysis of the Expression of CD133 mRNA in X01GBS Cells and X01GBD Cells The expression level of CD133 mRNA in X01GBS cells as a concentrated fraction of human glioblastoma stem cells, X01GBD cells as a concentrated fraction of cancer cells differentiated from the X01GBS cells, and normal WI-38 cells, was examined by electrophoresis following an RT-PCR method and a quantitative RT-PCR method. HPRT serving as a housekeeping gene was used as a control gene in RT-PCR.

Figure 5:
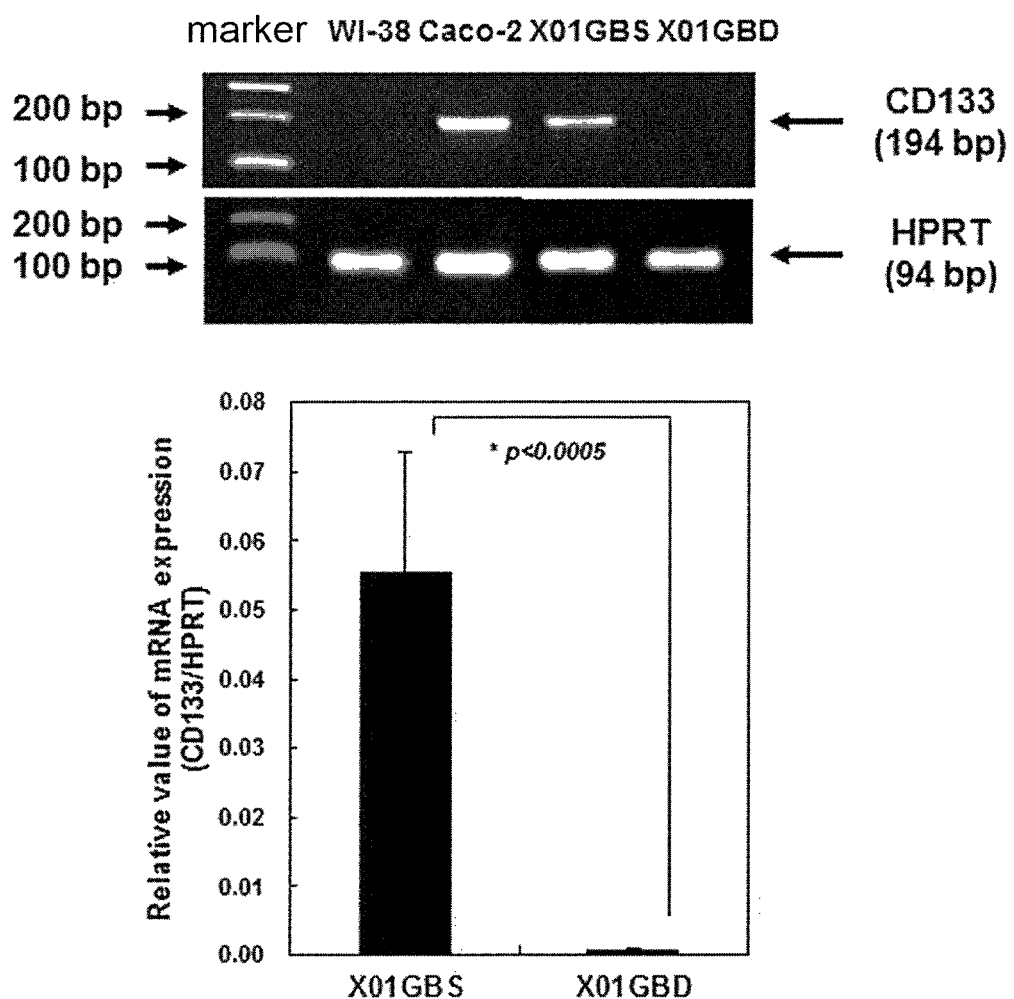
FIG. 5 shows the expression level of the mRNA of CD133 in each of normal cells WI-38 (fibroblast) that are CD133-negative cells, Caco-2 (colon cancer) that is a cell line positive to CD133 expression, X01GBS, and X01GBD. The photograph shows the results of electrophoresis performed after completion of an RT-PCR method, and the graph shows the results of quantitative RT-PCR. The term "HPRT" indicates a housekeeping gene HPRT used as a control gene. In the graph, the longitudinal axis indicates the ratio of the expression level of CD133 mRNA to the expression level of HPRT mRNA.

The experimental results are shown in FIG. 5. In the electrophoretic photographs by RT-PCR, prominent expressions of CD133 mRNA was observed in the X01GBS cells, as well as in Caco-2 cells used as positive control cells. In contrast, the expression of CD133 mRNA could not be detected in the normal WI-38 cells and the X01GBD cells. Moreover, the expression of CD133 mRNA was observed at a high level in the X01GBS cells as a result of the quantitative RT-PCT, whereas the expression level of CD133 mRNA in the X01GBD cells was at an extremely low level. A statistical difference (P<0.0005) was confirmed.

(Example 6) Analysis of the Expression of CD133 mRNA in X01GBS Cells and X01GBD Cells Moreover, X01GBS cells as a concentrated fraction of human glioblastoma stem cells were separated into CD133 expression-positive cells and CD133 expression-negative cells, using a cell sorter, and the expression level of CD133 mRNA in each fraction was then examined by RT-PCR and quantitative RT-PCR methods.

Figure 6:
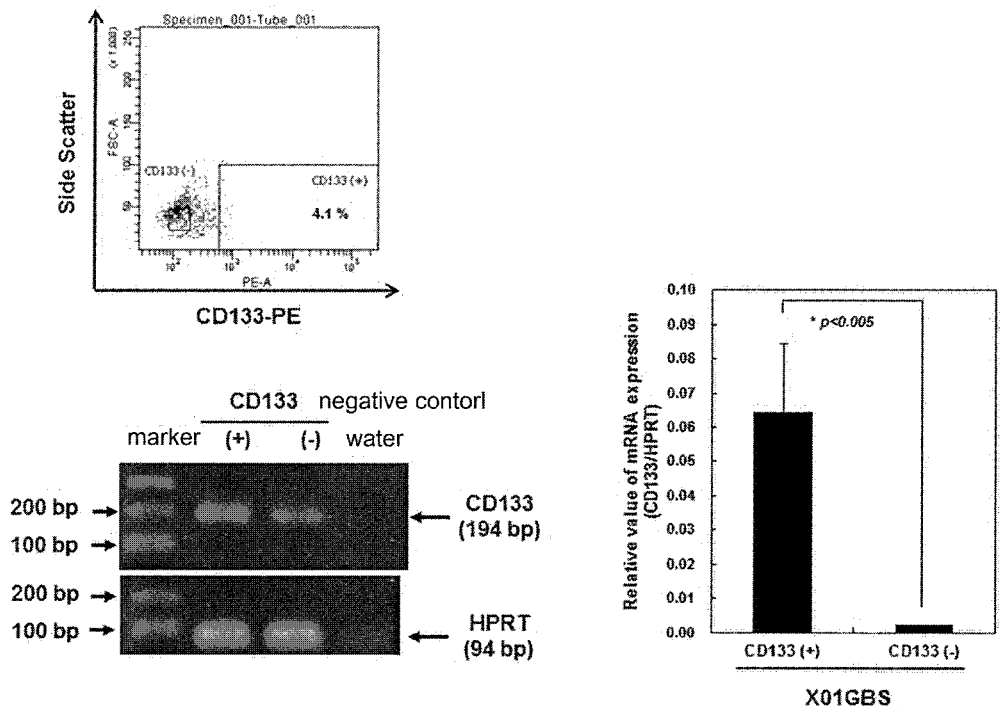
FIG. 6 shows the results obtained by separating CD133 expression positive cells and negative cells from X01GBS cells that are a concentrated fraction of human glioblastoma stem cells using a cell sorter, and then examining the expression level of CD133 mRNA in each fraction by RT-PCR and quantitative RT-PCR methods. The upper left view indicates each fraction separated with a cell sorter. The term "CD133(−)" indicates a fraction of CD133 expression negative cells, whereas the term "CD133(+)" indicates a fraction of CD133 expression positive cells. The lower left photograph shows the results of electrophoresis performed after completion of the RT-PCR method. The lower right graph shows the results of the quantitative RT-PCR. The term "HPRT" indicates a housekeeping gene HPRT used as a control gene. In the graph, the longitudinal axis indicates the ratio of the expression level of CD133 mRNA to the expression level of HPRT mRNA.

Representative results are shown in FIG. 6. The upper left view shows individual fractions separated using a cell sorter. The lower left view shows the results of the RT-PCR, and the lower right view shows the results of the quantitative RT-PCR. It could be confirmed that CD133 mRNA was expressed in the fraction of the separated CD133-positive cells at a higher level with a statistic difference (P<0.005) than in the fraction of the separated CD133-negative cells.

Figure 7:
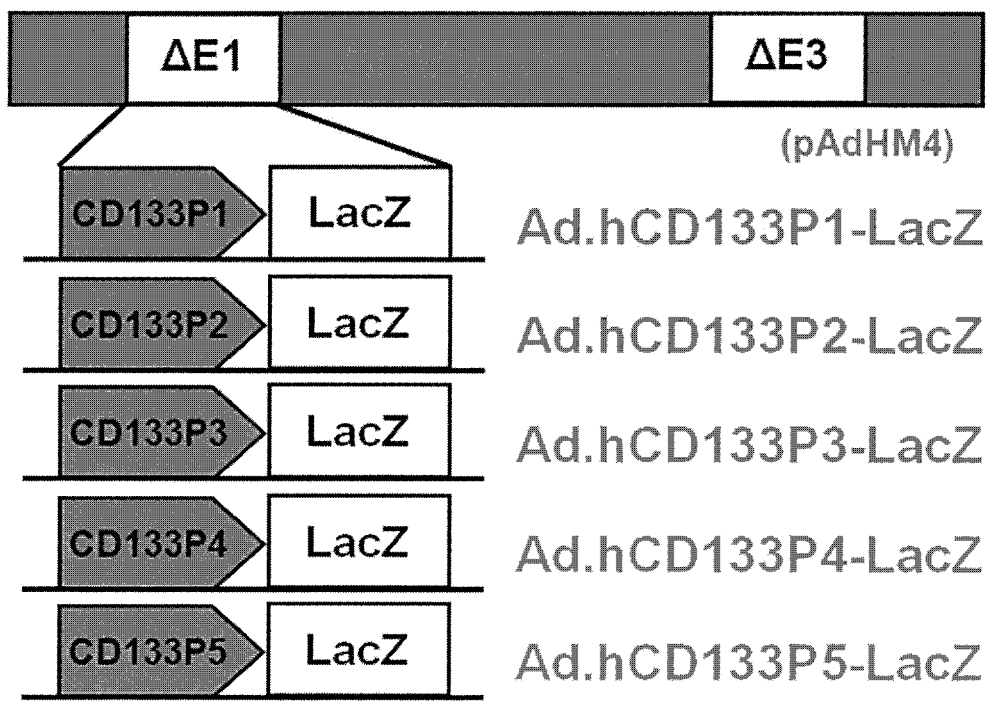
FIG. 7 shows a schematic view of an adenoviral vector used in reporter assay for measuring the activity of each CD133 promoter, and relevant names. LacZ was linked downstream of each CD133 promoter, and the obtained promoter was then incorporated into an adenoviral vector (pAdHM4) comprising a deletion in the E1 region (ΔE1).

(Example 7) Measurement of Activity of CD133 Promoters in Human Glioblastoma Stem Cells (X01GBS) (β-Gal Assay) (1) Construction of Adenoviral Vectors Used for Analysis of the Activity of CD133 Promoters Five types of promoters have been known with regard to human CD133. These promoters are referred to as promoter 1 (pr1; SEQ ID NO: 1), promoter 2 (pr2; SEQ ID NO: 2), promoter 3 (pr3; SEQ ID NO: 3), promoter 4 (pr4; SEQ ID NO: 4), and promoter 5 (pry; SEQ ID NO: 5), respectively (Sergey V. Shmelkov et al., BLOOD, 15 Mar. 2004, Vol. 103, No. 6). In order to measure the activity of each promoter in human glioblastoma stem cells (X01GBS), as shown in FIG. 7, LacZ was linked downstream of each of the five human CD133 promoters, and the thus produced promoter was then incorporated into a non-replicative adenoviral vector comprising a deletion in the E1 region, so as to construct an adenoviral vector for reporter assay. Hereafter, a vector formed by incorporating into an adenoviral vector, pr1 downstream of which LacZ was linked, is referred to as "Ad.hCD133pr1-LacZ." Likewise, vectors formed by incorporating into the ΔE1 of an adenoviral vector, pr2 to pry downstream of which LacZ was linked, are referred to as "Ad.hCD133pr2-LacZ," "Ad.hCD133pr3-LacZ," "Ad.hCD133pr4-LacZ, and "Ad.hCD133pr5-LacZ," respectively. In addition, these vectors are collectively referred to as "Ad.hCD133pr1-5-LacZ."

These vectors were constructed with reference to the method described in Chen S H, et al. (1995) PNAS 92 (7): 2577-2581.

(2) Measurement of the Activity of CD133 Promoters in Human Glioblastoma Stem Cells (X01GBS)

Conditions for culturing glioblastoma stem cells (X01GBS) were the same as those applied in Example 1(1). As a method of viral infection, cells to be infected with viruses were placed in a 1.5-ml tube, and were then centrifuged once. Thereafter, a supernatant was removed, and a culture solution containing viruses was added to the cell ppt, and viral infection was then carried out at 37° C. for 1 hour. During the infection, tapping or pipetting was performed every 15 minutes so as to increase the number of contacts between the viruses and the cells, thereby trying to increase infection efficiency.

The cells were infected with the above constructed adenoviral vector (Ad.hCD133pr1-5-LacZ) for reporter assay, using MOI (multiplicity of infection) that was the number of viruses to a single cell. That is, the human glioblastoma stem cells (X01GBS) were infected with Ad.hCD133pr1-5-LacZ at MCI of 30. Two days after completion of the infection, using Beta-galactosidase enzyme assay system (Promega, USA), the activity of each human CD133 promoter was measured in accordance with protocols included with the system, prepared by the manufacturer.

Figure 8:
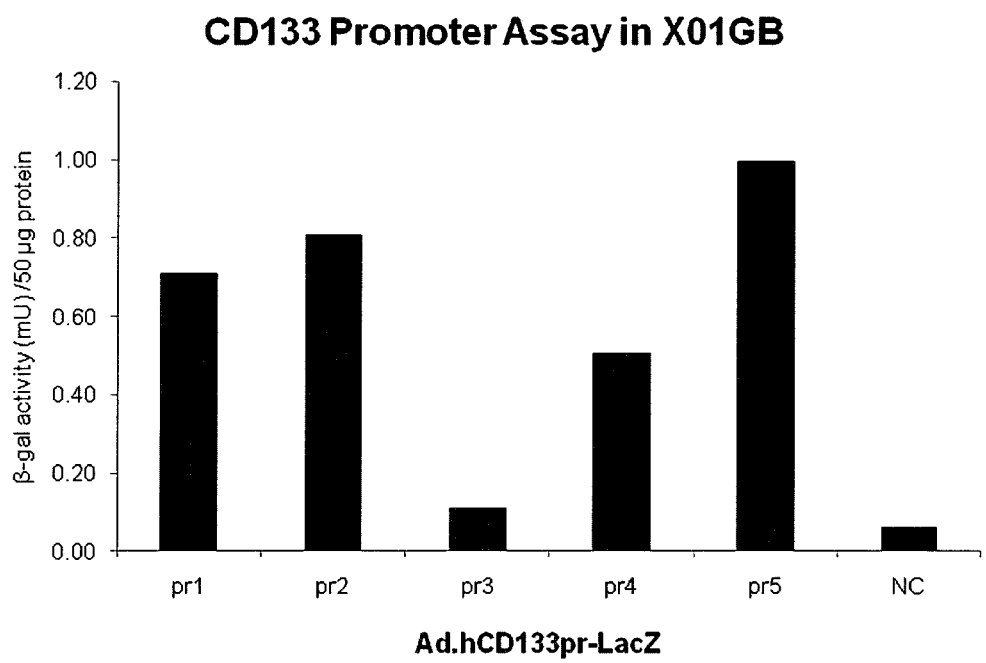
FIG. 8 shows the activity of each CD133 promoter in human glioblastoma stem cells (X01GBS). In the figure, the longitudinal axis indicates β-galactosidase activity (promoter activity), whereas the horizontal axis indicates the types of adenoviruses into which each promoter used for the expression of LacZ was incorporated. In the horizontal axis, pr1, pr2, pr3, pr4 and pry indicate, respectively, CD133 promoter 1, promoter 2, promoter 3, promoter 4 and promoter 5 (the same applies below in the following figures).

The results are shown in FIG. 8. As a result of the analysis of promoter activity by β-gal assay, it was demonstrated that, among the five promoters that control the expression of human CD133, promoter 1, 2, 4 and 5 have high activity, and that among them, promoter 5 has the highest transcriptional activity in the human glioblastoma stem cells (X01GBS).

Example 8

Furthermore, in order to examine the properties of the CD133 promoters more in detail, the same experiments regarding CD133 promoter assay as described above were performed in X01GBS cells as a concentrated fraction of human glioblastoma stem cells and in X01GBD cells as a concentrated fraction of cancer cells differentiated from the X01GBS cells. The experiment was carried out at N=3 for each group. As a positive control, an RSV promoter was used. As negative controls, an adenovirus into which no promoters had been inserted (ΔPr) and cells to which no adenoviruses had been added (NC) were used. The basic experimental methods were the same as those applied in Example 7, with the exception of the difference in the adenovirus infection method and simple devices made in each experimental step to increase sensitivity or the measurement of n-gal activity, so as to increase the sensitivity of the activity and make a detailed comparison.

Figure 9:
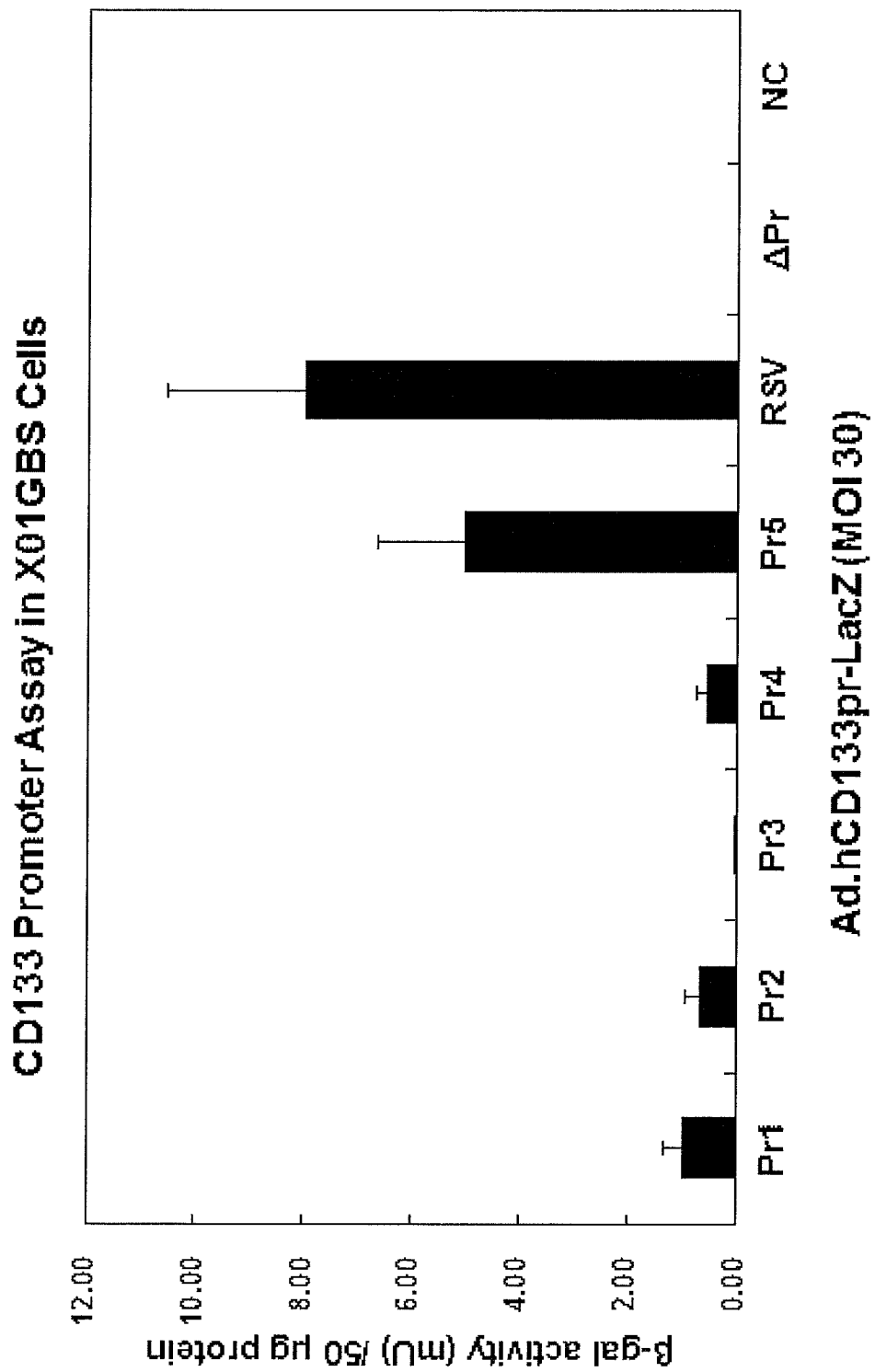
FIG. 9 shows the activity of each CD133 promoter in human glioblastoma stem cells (X01GBS). In the figure, the longitudinal axis indicates β-galactosidase activity (promoter activity), whereas the horizontal axis indicates the types of adenoviruses into which each promoter used for the expression of LacZ was incorporated.
Figure 10:
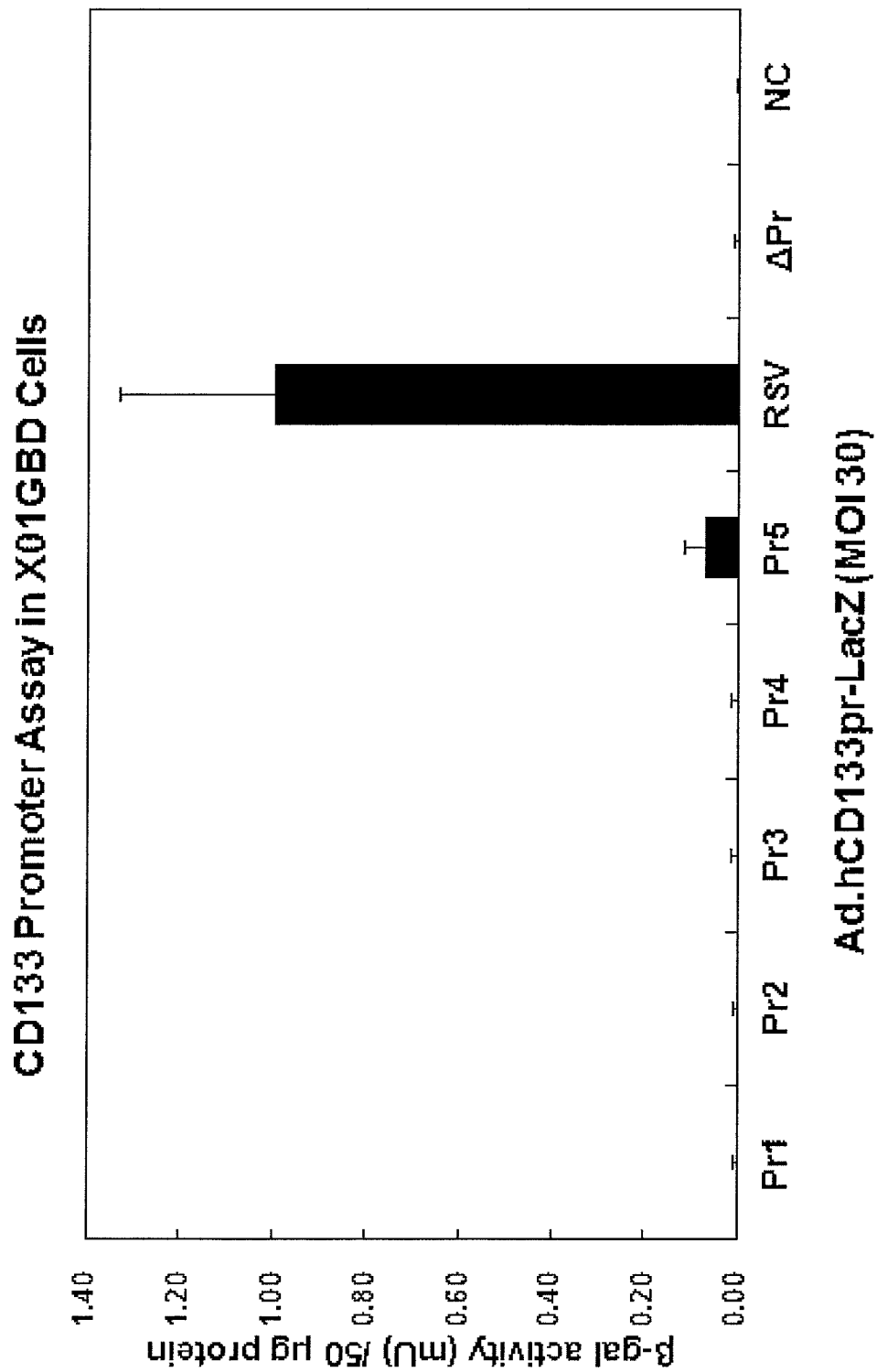
FIG. 10 shows the activity of each CD133 promoter in X01GBD cells that are a fraction obtained by concentrating cancer cells differentiated from human glioblastoma stem cells. In the figure, the longitudinal axis indicates β-galactosidase activity (promoter activity), whereas the horizontal axis indicates the types of adenoviruses into which each promoter used for the expression of LacZ was incorporated.

The average values and standard errors of the experimental results are shown in FIG. 9 (X01GBS cells) and FIG. 10 (X01GBD cells). As is shown in FIG. 9, in the X01GBS cells as a concentrated fraction of human glioblastoma stem cells, all of the promoters had various types of activity. As with the tendency shown in FIG. 8, promoter 5 had the highest activity, and promoters 1, 2 and 4 followed promoter 5, in terms of activity strength. The activity of promoter 3 was low. On the other hand, as shown in FIG. 10, in the X01GBD cells as a differentiated cancer cell fraction, promoter 5 had slight activity, but other promoters 1, 2, 3 and 4 had activity that was lower than the detection sensitivity (cutoff value). Moreover, the activity of promoter 5 was significantly lower than the value obtained in the X01GBS cells shown in FIG. 9, and it was almost a detection limit. Furthermore, in comparison with the RSV promoter used as a control as well, it became clear that the CD133 promoters have activity specific to the X01GBD cells as a concentrated fraction of cancer cells.

(Example 9) Measurement of the Activity of CD133 Promoters in Human Glioblastoma Stem Cells (X01GBS) (by Flow Cytometry)

Adenoviral vectors used for the analysis of the activity of CD133 promoters were constructed by the same method as that applied in Example 4, and each of the constructed vectors was introduced into human glioblastoma stem cells (X01GBS). Two days after completion of the infection, the expression of LacZ was detected by flow cytometry using FluoReporter lacZ Flow Cytometry Kit (Molecular Probes, Inc.) in accordance with protocols included with the kit, prepared by the manufacturer, thereby measuring the activity of the CD133 promoters. In addition, using an anti-CD133 antibody (mouse anti-human CD133/2 (293C3)-PE (Miltenyi Biotec)), CD133(+) cells were labeled and then measured.

Figure 11:
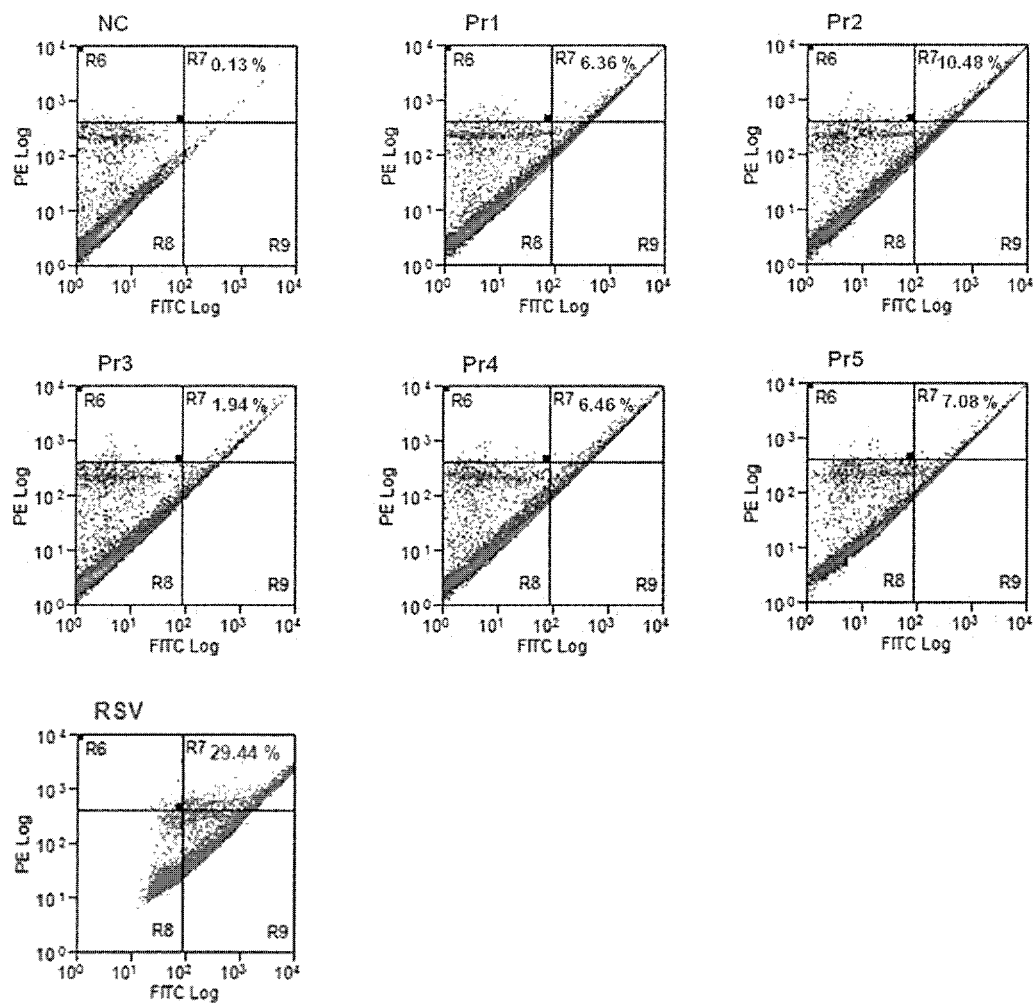
FIG. 11 shows the results obtained by confirming by flow cytometry, the correlation of the activity of each of CD133 promoters and a non-specific RSV promoter used as a control, with CD133(+) cells in human glioblastoma stem cells (X01GBS). In the figure, the horizontal axis indicates LacZ activity (the activity of each CD133 promoter), whereas the longitudinal axis indicates CD133(+) cells with a PE-labeled anti-CD133 antibody. The numerical value (%) in FIG. 6 indicates the ratio of cells correlating with the inside of the upper right region R7.
Figure 12:
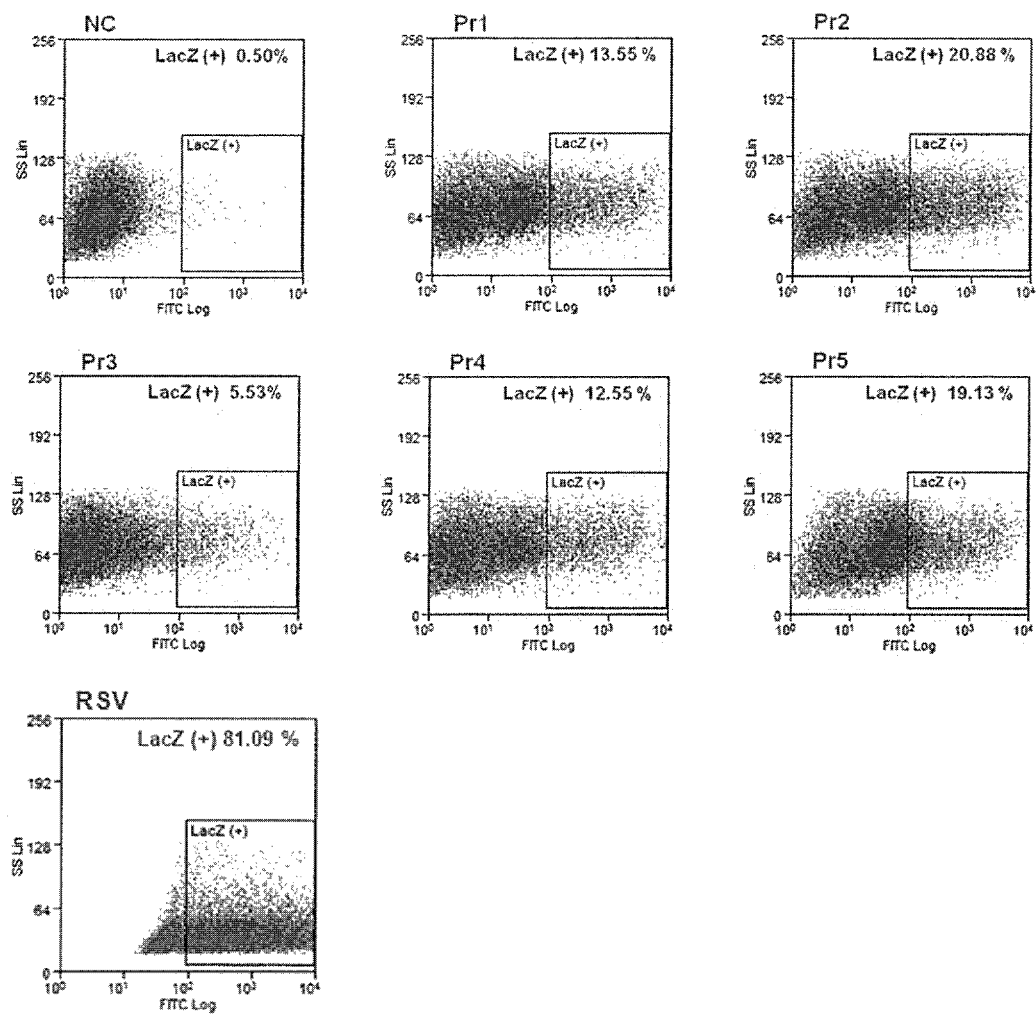
FIG. 12 is a view showing a comparison among the activity of individual CD133 promoters and the activity of a non-specific RSV promoter used as a control in human glioblastoma stem cells (X01GBS). In the figure, the horizontal axis indicates LacZ activity (the activity of each CD133 promoter), whereas the longitudinal axis indicates side scatter (SS). The numerical value (%) in FIG. 12 indicates the ratio of the number of LacZ-expressing cells contained in the region enclosed with the square to the total cell number.

The correlation between each CD133 promoter activity in human glioblastoma stem cells (X01GBS) and the expression level of CD133 on the cell surface is shown in FIG. 11. In the figure, the horizontal axis indicates LacZ activity (CD133 promoter activity), and the longitudinal axis indicates an anti-CD133 antibody labeled with PE (the expression level of CD133 on the cell surface). The numerical value (%) shown in FIG. 11 indicates the percentage of cells distributing in the upper right region R7. As shown in FIG. 11, it became clear that the activity of each CD133 promoter correlates with the expression level of CD133. On the other hand, using, as a control, a representative RSV promoter that constantly (ubiquitously) exhibits strong expression, the same experiment as described above was carried out. As a result, the activity of the RSV promoter was observed with no correlation with endogenous CD133 expression, namely, non-specifically to CD133. Accordingly, it was found that CD133 promoters 1-5 become activated with a correlation with endogenous CD133 expression, namely, specifically to CD133 expression. Moreover, FIG. 12 is a view showing a comparison made among the activity of individual CD133 promoters in the X01GBS cells. In FIG. 12, the horizontal axis indicates LacZ activity (CD133 promoter activity), and the longitudinal axis indicates side scatter (SS). The numerical value (%) shown in FIG. 12 indicates the percentage of cells distributing in the region R6 enclosed with the square. From there results, it was demonstrated that, among the CD133 promoters, promoter 2 and promoter 5 exhibited particularly high activity.

Example 10

Furthermore, the activity of each CD133 promoter in X01GBS cells as a concentrated fraction of human glioblastoma stem cells and in X01GBD cells as a concentrated fraction of the differentiated cancer cells was examined by flow cytometry.

Figure 13:
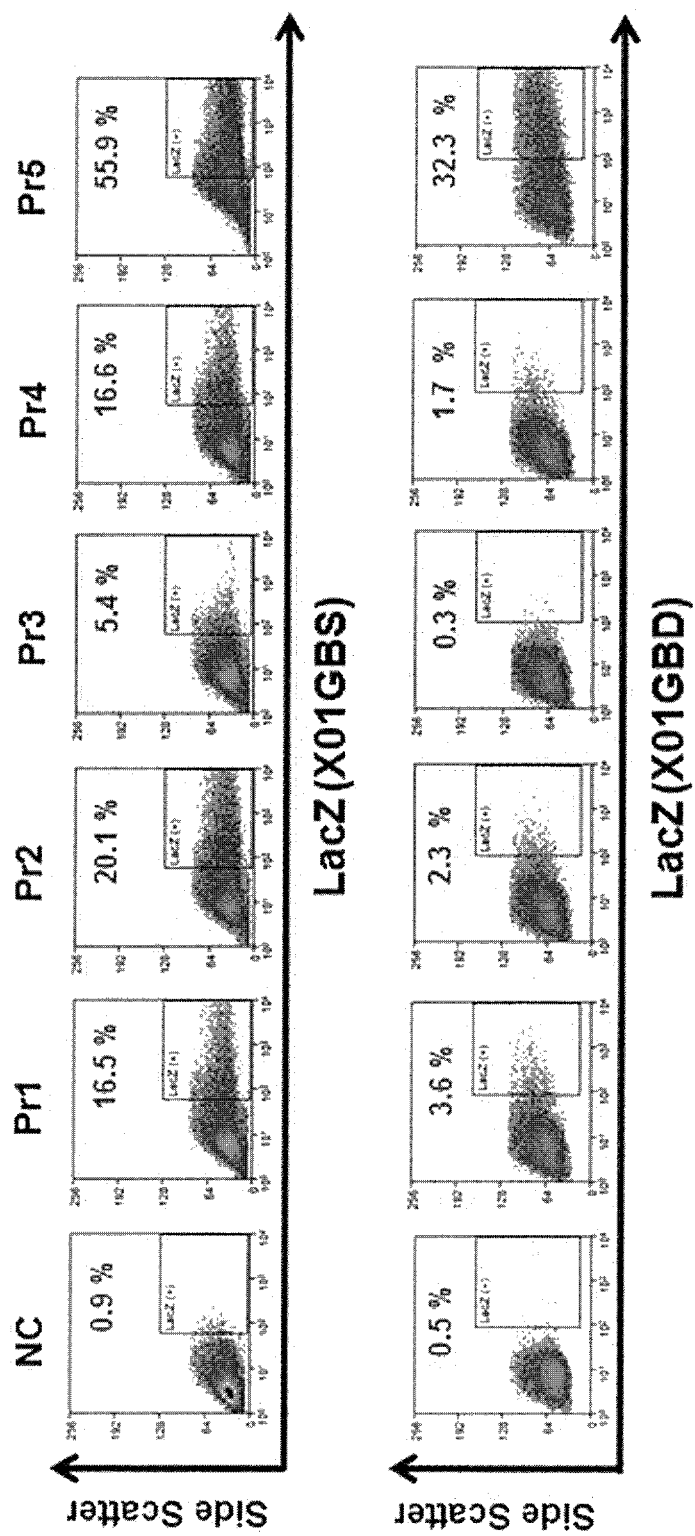
FIG. 13 is a view showing a comparison among the activity of individual CD133 promoters in human glioblastoma stem cells (X01GBS) and in X01GBD cells that are a fraction obtained by concentrating cancer cells differentiated from the human glioblastoma stem cells. In the figure, the horizontal axis indicates LacZ activity (the activity of each CD133 promoter), whereas the longitudinal axis indicates side scatter (SS). The numerical value (%) in FIG. 13 indicates the ratio of the number of LacZ-expressing cells contained in the region enclosed with the square to the total cell number.

The results are shown in FIG. 13. In the figure, the horizontal axis indicates LacZ activity (the activity of each CD133 promoter), and the longitudinal axis (SS Lin) indicates the side scatter (SS), which reflects cell morphology, or internal cell structure such as a nucleus and a granule. The numerical value (%) shown in FIG. 13 indicates the activity of each CD133 promoter (LacZ positive rate). As such, in all of CD133 promoters 1 to 5, the percentage of cells exhibiting CD133 promoter activity was higher in the X01GBS cells as a concentrated fraction of cancer stem cells than in the X01GBD cells. Moreover, with regard to the ratio of cells exhibiting the activity of each of the CD133 promoters 1 to 5 in the X01GBS cells, the ratio of cells exhibiting the activity of CD133 promoter 5 was the highest, and the ratios of cells exhibiting the activity of CD133 promoters 1, 2 and 4 were almost the same levels (wherein promoter 2 was slightly stronger among them). The ratio of cells exhibiting the activity of CD133 promoter 3 was the lowest. This tendency correlated well with the strength of each promoter activity shown in FIGS. 8 and 9.

Figure 14:
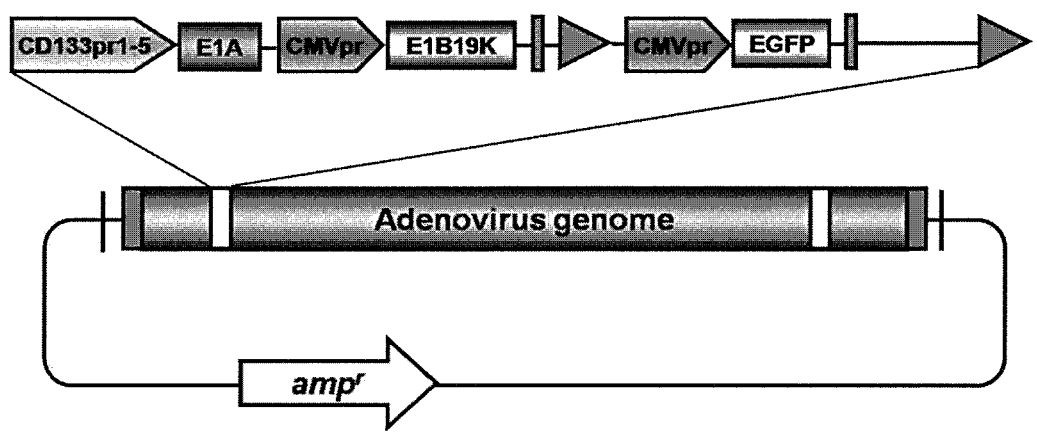
FIG. 14 shows the structure of an adenoviral vector that replicates specifically in cancer stem cells (which is CD133-reactive m-CRA referred to as "Ad.hCD133pr5-m-CRA"; the same applies below). In the figure, the term "CD133 pr 1 to 5" indicate any one of CD133 promoters 1 to 5.

(Example 11) Construction of Cancer Stem Cell-Specific-Replication-Type Adenoviral Vectors (1) Construction of Cancer Stem Cell-Specific-Replication-Type Adenoviral Vectors In accordance with the method described in International Publication No. WO 2005/012536, as shown in FIG. 14, five CD133 promoters were incorporated into the site in front of the E1A region that is an early gene essential for replication of adenovirus, so as to construct a cancer stem cell-specifically replication-controlled adenoviral vector (CD133-reactive m-CRA), which is capable of killing or causing damage specifically to a CD133 expression tumor. Hereafter, CD133-reactive m-CRA, into which CD133 promoter 1 has been incorporated, is referred to as "hCD133pr1-m-CRA." With regard to promoters 2 to 5, relevant recombinant vectors are referred to in the same manner as described above. Moreover, CD133-reactive m-CRA, into which each of the 5 types of CD133 promoters has been incorporated, is collectively referred to as "hCD133pr1-5-m-CRA."

(2) Measurement of Efficiency of Introducing Adenoviral Vector into Human Glioblastoma Stem Cells The same conditions for culturing glioblastoma stem cells (X01GBS) as those in Example 1(1) were applied herein. In addition, the same viral infection method as that in Example 4(2) was applied herein.

The vector was constructed with reference to the method described in Chen S H, et al. (1995) PNAS 92 (7): 2577-2581.

Human glioblastoma stem cells (X01GBS) were infected with that above-constructed non-replicative adenoviral vector (Ad.CA-EGFP) at MOI of 30. Twenty-four hours after completion of the infection, the efficiency of introducing Ad.CA-EGFP into the human glioblastoma stem cells (X01GBS) was measured. Specifically, since an EGFP fluorescent protein gene had been introduced into the site downstream of the CA promoter in Ad.CA-EGFP, the expression of EGFP could be confirmed as a result of the infection with the Ad.CA-EGFP.

Figure 15:
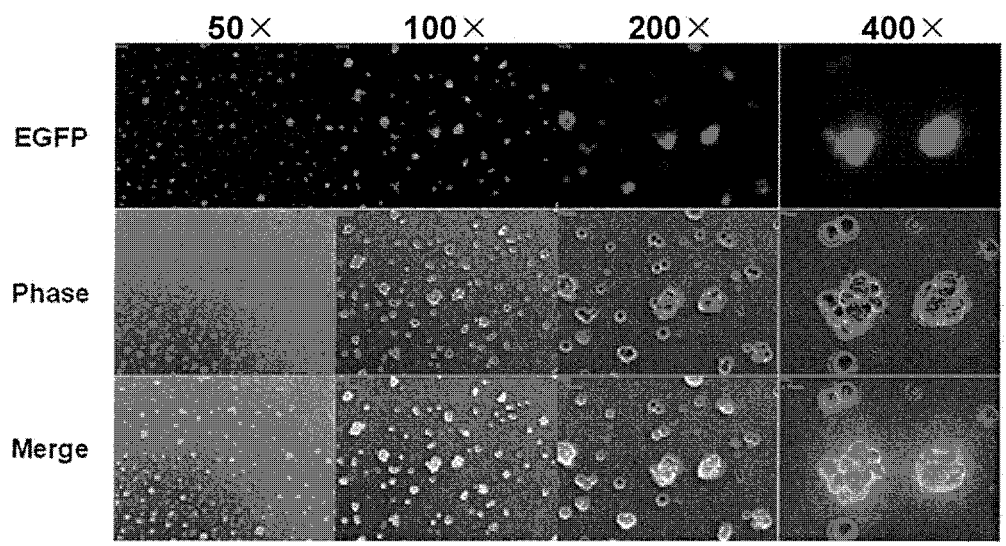
FIG. 15 shows the efficiency of introducing an adenovirus into human glioblastoma stem cells (X01GBS). The figure includes photographs taken 24 hours after infection of the X01GBS cells with a non-replicative adenoviral vector (Ad.CA-EGFP). In the figure, beginning at the top, the term "EGFP" indicates a photograph showing the expression of EGFP detected, the term "Phase" indicates a microphotograph, and the term "Merge" indicates a photograph formed by synthesizing the two types of photographs, showing the expression of EGFP in the cells (the same applies to FIG. 16). In addition, the numerical value above each photograph indicates the magnification applied in the observation.

The results obtained by measuring the efficiency of introducing the non-replicative adenoviral vector into human glioblastoma stem cells are shown in FIG. 15. Twenty-four hours after completion of the infection, the expression of EGFP was observed in almost all of the X01GBS cells. Thus, it was confirmed that the adenoviral vector (Ad.CA-EGFP) is efficiently introduced into the glioblastoma stem cells.

(3) Measurement of the Effect of hCD133pr5-m-CRA to Kill or Cause Damage to X01GBS Cells The same conditions for culturing glioblastoma stem cells (X01GBS) as those in Example 1(1) were applied herein. The same viral infection method as that in Example 4(2) was applied herein.

Human glioblastoma stem cells (X01GBS) were infected with the above-constructed hCD133pr5-m-CRA at MOI of 3. One, two, three, four and five days after completion of the infection, the hCD133pr5-m-CRA-introduced human glioblastoma stem cells (X01GBS) were observed under a microscope.

Figure 16:
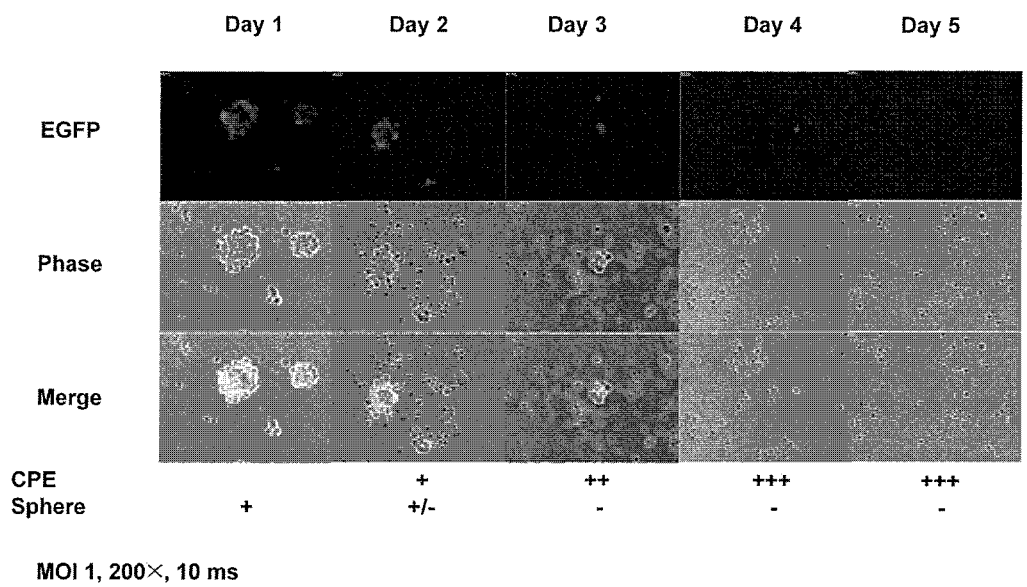
FIG. 16 shows the cytotoxic effects of hCD133pr5-m-CRA on the human glioblastoma stem cells (X01GBS) based on cell morphology. The figure shows the results obtained by infecting X01GBS with Ad.hCD133pr5-m-CRA at MOI of 1, and then observing the cells under a 200× microscope, 1, 2, 3, 4 and 5 days after the infection. The numerical value (Day) at the top of the figure indicates the number of days elapsed after the viral infection. The term "CPE" at the bottom of the figure indicates cytopathic effect, and the term "Sphere" indicates the degree of cell mass formation.

As shown in FIG. 16, it became clear that CD133pr5-m-CRA can kill or cause damage to the X01GBS cells. When compared with the case of infecting the cells with the adenovirus Ad.RSV-dE1.3 or Ad.CA-EGFP (the results are not shown), it was confirmed that hCD133pr5-m-CRA caused CPE to the cells 2 days after the infection and destroyed the cell mass (sphere) structure of the cancer stem cells. In addition, 5 days after the infection, a majority of the cells infected with hCD133pr5-m-CRA were dead. From these results, it was demonstrated that CD133pr5-mCRA has an ability to kill or cause damage to human glioblastoma stem cells (X01GBS).

(4) Measurement of the Number of Surviving X01GBS Cells after Completion of Viral Infection (WST Assay)

The same conditions for culturing glioblastoma stem cells (X01GBS) as those in Example 1(1) were applied herein. The same viral infection method as that in Example 4(2) was applied herein.

Human glioblastoma stem cells (X01GBS) were infected with the above-constructed hCD133pr5-m-CRA, and with Ad.CA-EGFP and Ad.RSV-dE1.3 used as negative controls, each at MOI of 1, 3 and 10. A non-replicative adenoviral vector (Ad.RSV-dE1.3) is a vector formed by incorporating an RSV promoter into a non-replicative adenoviral vector comprising a deletion in the E1 and E3 regions, and is used to evaluate the toxicity of the virus itself caused by the viral infection (different from therapeutic effects) in adenovirus infection experiments. Five days after completion of the infection, using WST-8 cell proliferation assay kit (Nakarai), the number of surviving cells was counted.

Figure 17:
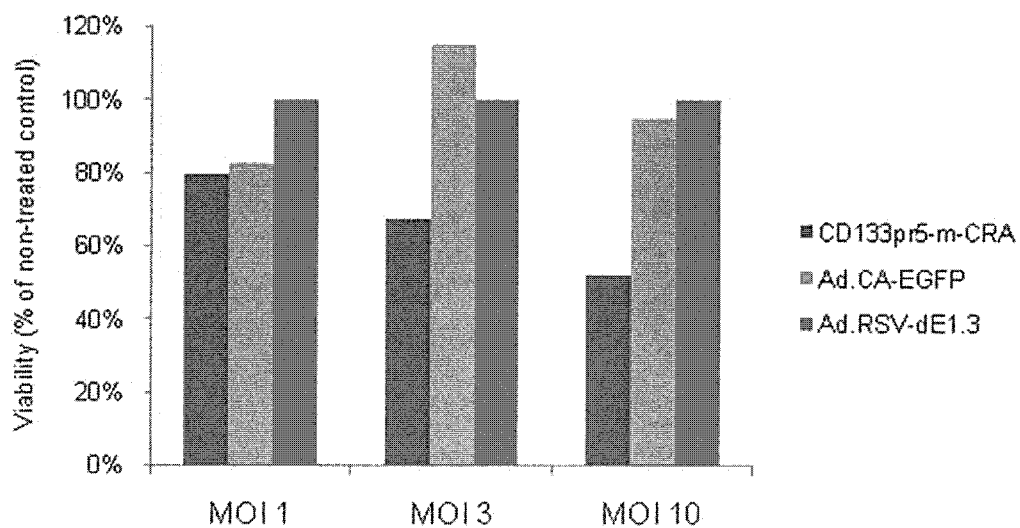
FIG. 17 is a graph showing the cytotoxic effects of Ad.hCD133pr5-m-CRA on human glioblastoma stem cells (X01GBS) based on the number of surviving cells. The graph shows the results obtained by infecting human glioblastoma stem cells (X01GBS) with Ad.hCD133pr5-m-CRA, Ad.CA-EGFP and Ad.RSV-dE1.3 at MOIs of 1, 3 and 10, and then counting the number of surviving cells on the $5^{th}$ day after the infection. In the figure, the longitudinal axis indicates the percentage (%) of surviving cells obtained by comparing with a non-treated group, whereas the horizontal axis indicates conditions for viral infection (MOI).

The results are shown in FIG. 17. It was demonstrated that hCD133pr5-m-CRA kills or causes damage to X01GBS cells, particularly when it is used at MOI of 3 and 5. On the other hand, such effects were not confirmed from Ad.CA-EGFP and Ad.RSV-dE1.3.

(Example 12) Cytotoxic Activity of hCD133pr-m-CRA on X01GBS and X01GBD

Furthermore, in order to demonstrate that the therapeutic effects of hCD133pr-m-CRA to kill or cause damage to cells are specific to cancer stem cells, the same experiment was carried out not only on X01GBS as a concentrated fraction of human glioblastoma stem cells, but also on X01GBD as a concentrated fraction of the differentiated cancer cells, and the results were then compared with each other.

Figure 18:
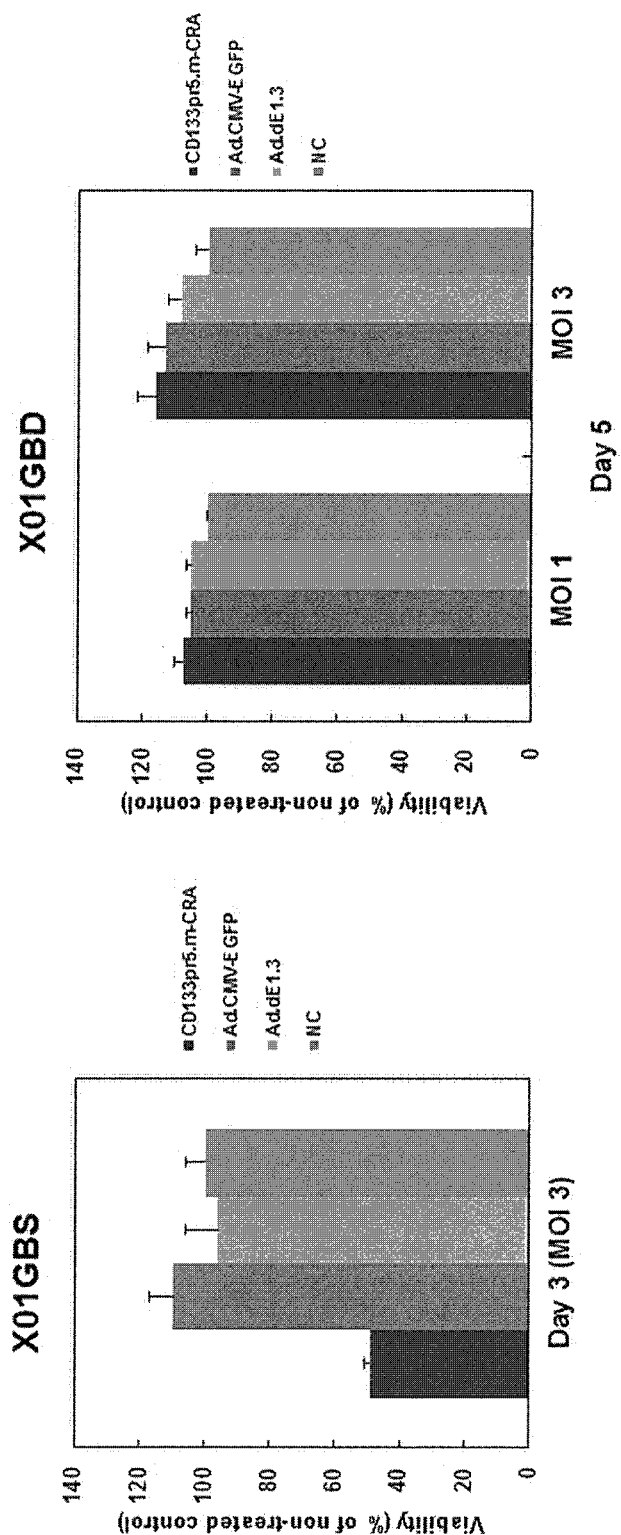
FIG. 18 is a graph showing the cytotoxic effects of Ad.hCD133pr5-m-CRA on human glioblastoma stem cells, X01GBS cells, and X01GBD that is a fraction obtained by concentrating cancer cells differentiated from human glioblastoma stem cells, based on the number of surviving cells. In the figure, the longitudinal axis indicates the percentage (%) of the number of surviving cells obtained by comparing with a non-treated group, whereas the horizontal axis indicates conditions for viral infection (MOI).

The results are shown in FIG. 18. The left view shows the results obtained by infecting human glioblastoma stem cells (X01GBS) with hCD133pr5-m-CRA, Ad.CMV-EGFP and with Ad.RSV-dE1.3 at MOI of 3, and then counting the number of surviving X01GBS cells on the $3^{rd}$ day. The right view shows the results obtained by infecting differentiated human glioblastoma stem cells (X01GBD) with hCD133pr5-m-CRA, Ad.CMV-EGFP and with Ad.RSV-dE1.3 at MOI of 1 and 3, and then counting the number of surviving X01GBD cells on the 5$^{th}$ day. In the figure, the longitudinal axis indicates the percentage (%) of the number of surviving cells in comparison with a non-treated group, and the horizontal axis indicates conditions for viral infection (MOI). As shown in FIG. 18, only hCD133pr5-m-CRA exhibited significant cytotoxic effects on the X01GBS as a concentrated fraction of human glioblastoma stem cells. On the other hand, hCD133pr5-m-CRA exhibited almost no effects on the X01GBD as a concentrated fraction of the differentiated cancer cells. Specifically, it was found that hCD133pr5-m-CRA exhibits viral replication and cytotoxic effects specifically in cancer stem cells.

(Example 13) Confirmation of Ability of X01GBS to Form Tumor

Further, in order to confirm that X01GBS as a concentrated fraction of human glioblastoma stem cells and X01GBD as a concentrated fraction of the differentiated cancer cells have their own properties, an experiment was carried out to transplant the cells of each fraction into NOD/SCID immunodeficiency mice, so as to examine their ability to form a tumor. $1 \times 10^6$ or $1 \times 10^5$ of X01GBS cells were subcutaneously transplanted at 4 sites in each NOD/SCID immunodeficiency mouse, and $1 \times 10^6$ of differentiated X01GBD cells were subcutaneously transplanted at 3 sites in each NOD/SCID immunodeficiency mouse. Ten weeks after completion of the subcutaneous transplantation, the ratio of formation of nodules that could be recognized with naked eyes was evaluated.

Figure 19:
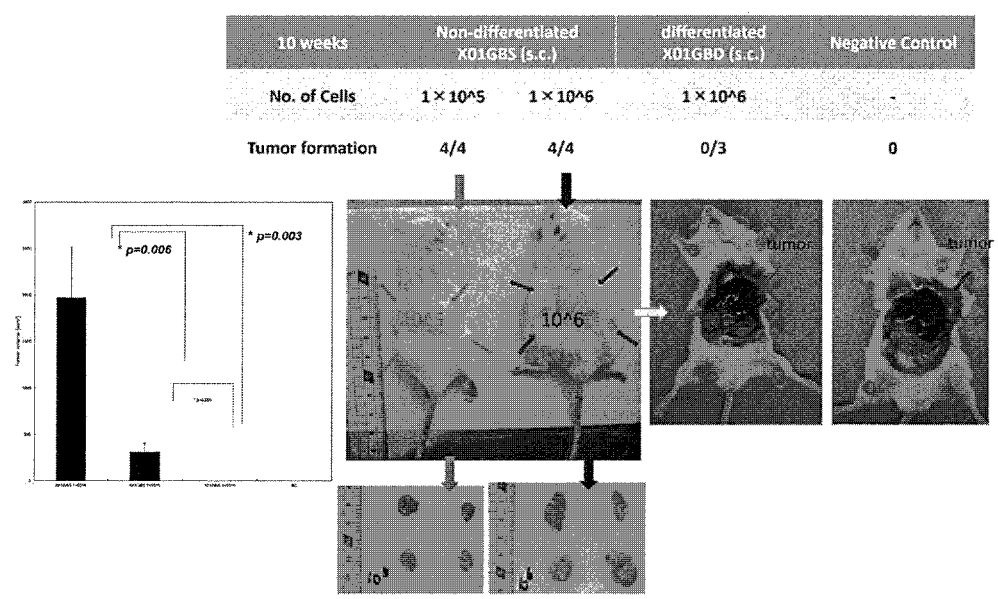
FIG. 19 shows the results obtained by subcutaneously transplanting $1\times10^6$ or $1\times10^5$ of X01GBS cells at four sites in a NOD/SCID immunodeficiency mouse and also subcutaneously transplanting $1\times10^6$ of differentiated X01GBD cells at three sites in a NOD/SCID immunodeficiency mouse, and then, 10 weeks after the subcutaneous transplantation, evaluating the percentage of formation of nodules that can be recognized with naked eyes. In the graph, the longitudinal axis indicates the volume of a tumor ($mm^3$), whereas the horizontal axis indicates the type and number of the transplanted cells. The three types of photographs all show the results of the NOD/SCID immunodeficiency mice into which X01GBS cells ($1\times10^6$, right; and $1\times10^5$, left) were transplanted. The photographs below show tumor masses collected from individual mice.

The results are shown in FIG. 19. In the case of the mice into which the X01GBS cells had been transplanted, formation of tumors was observed in all of the mice regardless of the number of the cells transplanted. In contrast, in the case of transplantation of the X01GBD cells, even if the cells were transplanted in an amount 10 times higher ($1 \times 10^6$) into the mice, no formation of tumors was observed in all of the mice. Thereby, the ability of undifferentiated X01GBS cells to form tumors was confirmed. Further, the mice were subjected to euthanasia and the subsequent skin incision, so that nodules formed under the skin were extracted and observed. As a result, it was also confirmed that tumors were formed with no doubt (namely, that was not a reaction such as inflammation).

From the above-mentioned results, it was clarified that since hCD133pr5-m-CRA replicates in cancer stem cells and expresses an EGFP gene inserted downstream of the CMV promoter, this vector can visualize the cancer stem cells. Thereby, hCD133pr5-m-CRA enables confirmation of the location or measurement of abundance of the cancer stem cells, and thus, it can be utilized for evaluation of therapeutic effects. In addition, since hCD133pr5-m-CRA has an ability not only to visualize cancer stem cells, but also to kill or cause damage to the cancer stem cells, it was demonstrated that this vector also has therapeutic effects.

From the above described results, it was demonstrated that a newly developed replication-controlled adenoviral vector, CD133-reactive m-CRA, is targeted to cancer stem cells, and is able to infect glioblastoma stem cells (X01GBS) and kill or cause damage thereto. Moreover, by loading the replication-controlled adenoviral vector CD133-reactive m-CRA with an EGFP gene, the effect of visualizing the treatment after completion of the viral infection can also be obtained. The cancer stem cell-targeting adenoviral vector of the present invention is actually directed towards the radical treatment of refractory cancer and prevention of the recurrence of such cancer (practical realization in clinical sites).

INDUSTRIAL APPLICABILITY

Since the viral vector of the present invention can be used in the treatment, prevention, metastasis suppression, and diagnosis of cancer, which is targeted to cancer stem cells, it can be used in the field of therapeutic agents and diagnostic agents.

The invention claimed is:

1. A method for expressing a desired gene specifically in a brain cancer stem cell, comprising:
administering a viral vector which comprises a CD133 promoter operably linked to the desired gene, wherein the desired gene is E1A, E1M24, E1AΔ24, E1B, or E1BΔ55K, wherein the viral vector expresses the desired gene specifically in the brain cancer stem cell, wherein the brain cancer stem cell is a glioblastoma cancer stem cell.

2. The method of claim 1, wherein the viral vector is oncolytic.

3. The method of claim 1, wherein the viral vector is adenovirus, herpes simplex virus, myxoma virus, reovirus, vesicular stomatitis virus, Newcastle disease virus, vaccinia virus, RS virus, Sendai virus, measles virus, Coxsackie virus, or Seneca Valley virus.

4. The method of claim 3, wherein the viral vector is adenovirus.

5. The method of claim 4, wherein the desired gene is the E1A or E1B gene.

6. The method of claim 5, wherein the E1A gene lacks the Rb-binding region (E1AΔ24) or the E1B gene lacks the p53-binding region (E1BΔ55K).

7. The method of claim 1, further comprising an exogenous cancer-specific promoter.

8. The method of claim 1, wherein the viral vector further comprises a marker gene or/and a cytotoxic gene.

9. The method of claim 5, wherein the adenoviral vector is selected from the following (a) to (c):
(a) an adenoviral vector having the following transcription units:
(a1) a CD133 transcription unit consisting of a CD133 promoter and the E1A gene or E1AΔ24 gene operably linked downstream of said promoter,
(a2) a transcription unit consisting of a eukaryotic cell promoter, a cancer-specific promoter or CD133 promoter, and the E1B gene or E1BΔ55K gene operably linked downstream of said promoter, or a transcription unit consisting of an E1BΔ19K gene operably linked downstream of a cancer-specific promoter, and
(a3) optionally, an additional transcription unit consisting of a eukaryotic cell promoter, a cancer-specific promoter or CD133 promoter, and a marker gene or cytotoxic gene operably linked downstream of said promoter;
(b) an adenoviral vector having the following transcription units:
(b1) a transcription unit consisting of a eukaryotic cell promoter, a cancer-specific promoter or CD133 promoter, and the E1A gene or E1AΔ24 gene operably linked downstream of said promoter,
(b2) a CD133 transcription unit consisting of a CD133 promoter and the E1B gene or E1BΔ55K gene operably linked downstream of said CD133 promoter, and
(b3) optionally, an additional transcription unit consisting of a eukaryotic cell promoter, a cancer-specific promoter or CD133 promoter, and a marker gene or cytotoxic gene operably linked downstream of said promoter; and
(c) an adenoviral vector having the following transcription units:
(c1) a transcription unit consisting of a eukaryotic cell promoter, a cancer-specific promoter or CD133 promoter, and the E1A gene or E1AΔ24 gene operably linked downstream of said promoter,
(c2) a transcription unit consisting of a eukaryotic cell promoter, a cancer-specific promoter or CD133 promoter, and the E1B gene or E1BΔ55K gene operably linked downstream of said promoter, and
(c3) a CD133 transcription unit consisting of a CD133 promoter and a marker gene or cytotoxic gene operably linked downstream of said CD133 promoter.

10. The method of claim 1, wherein the desired gene is a marker gene or cytotoxic gene.

11. The method of claim 10, wherein the viral vector further comprises an exogenous cancer-specific promoter.

12. The method of claim 1, wherein the desired gene comprises a cytotoxic gene and a marker gene.

13. The method of claim 10, wherein the viral vector is oncolytic virus.

14. The method of claim 1, wherein the CD133 promoter is any one of nucleic acid molecule selected from the following (i) to (iv):
(i) a nucleic acid molecule comprising the nucleotide sequence of any one of SEQ ID NOS: 1 to 5,
(ii) a nucleic acid molecule comprising a nucleotide sequence having 85% homology to any one of SEQ ID NOS: 1 to 5,
(iii) a nucleic acid molecule which can hybridize under stringent conditions with the nucleic acid molecule having the nucleotide sequence of any one of SEQ ID NOS: 1 to 5 or having complement of said sequence, and
(iv) a nucleic acid molecule having a nucleotide sequence of any one of SEQ ID NOS: 1 to 5, wherein a part of nucleotide is substituted or deleted, or additional nucleotide is added or inserted.

15. The method of claim 1, wherein the CD133 promoter is promoter 5 of CD133 promoter.

16. A method for specifically damaging a brain cancer stem cell, comprising administering a viral vector which comprises a CD133 promoter operably linked to the desired gene, wherein the desired gene is E1A, E1M24, E1AΔ24, E1B, or E1BΔ55K, wherein the viral vector expresses said desired gene specifically in the cancer stem cell, and wherein the desired gene is a gene encoding a protein which is essential for replication of virus and the viral vector can replicate specifically in a cancer stem cell, or the desired gene is cytotoxic gene, wherein the brain cancer stem cell is a glioblastoma cancer stem cell.

* * * * *